United States Patent
Zhang et al.

(10) Patent No.: US 11,156,619 B2
(45) Date of Patent: Oct. 26, 2021

(54) FLUORESCENT PH SENSORS AND METHODS OF PREPARING THEM

(71) Applicant: Arizona Board of Regents, on behalf of Arizona State University, Scottsdale, AZ (US)

(72) Inventors: Liqiang Zhang, Chandler, AZ (US); Xiangxing Kong, Tempe, AZ (US); Yanqing Tian, Tempe, AZ (US); Deirdre Meldrum, Phoenix, AZ (US); Fengyu Su, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/479,373

(22) PCT Filed: Jan. 19, 2018

(86) PCT No.: PCT/US2018/014519
§ 371 (c)(1),
(2) Date: Jul. 19, 2019

(87) PCT Pub. No.: WO2018/136794
PCT Pub. Date: Jul. 26, 2018

(65) Prior Publication Data
US 2019/0360984 A1   Nov. 28, 2019

Related U.S. Application Data

(60) Provisional application No. 62/448,761, filed on Jan. 20, 2017.

(51) Int. Cl.
| | | |
|---|---|---|
| *G01N 21/64* | (2006.01) | |
| *G01N 33/84* | (2006.01) | |
| *C07D 471/16* | (2006.01) | |
| *C08F 220/58* | (2006.01) | |
| *C12Q 1/02* | (2006.01) | |
| *G01N 31/22* | (2006.01) | |
| *G01N 33/50* | (2006.01) | |
| *G01N 21/77* | (2006.01) | |

(52) U.S. Cl.
CPC ........... *G01N 33/84* (2013.01); *C07D 471/16* (2013.01); *C08F 220/58* (2013.01); *C12Q 1/02* (2013.01); *G01N 21/64* (2013.01); *G01N 21/6428* (2013.01); *G01N 31/221* (2013.01); *G01N 33/5005* (2013.01); *G01N 2021/6439* (2013.01); *G01N 2021/7786* (2013.01)

(58) Field of Classification Search
CPC ............... G01N 31/221; G01N 33/84; G01N 2021/7786; G01N 21/64; G01N 21/80; G01N 21/6428; G01N 2021/6432; G01N 2021/6439; G01N 2021/644; C07D 471/16

USPC ............................................................ 422/68
See application file for complete search history.

(56) References Cited

U.S. PATENT DOCUMENTS

| | | |
|---|---|---|
| 8,748,192 B2 | 6/2014 | Tian et al. |
| 10,156,573 B2 | 12/2018 | Tian et al. |
| 2016/0202247 A1 | 7/2016 | Tian et al. |

FOREIGN PATENT DOCUMENTS

CN          102344449 A   *   2/2012

OTHER PUBLICATIONS

Tian et al. "A series of naphthalimide derivatives as intra and extracellular pH sensors" Biomaterials 31 (2010) 7411-7422 (Year: 2010).*
Zhou et al. "A pH sensitive ratiometric fluorophore and its application for monitoring the intracellular and extracellular pHs simultaneously" Mater. Chem. B, 2013, 1, 661 (Year: 2013).*
Zhang, L. et al. "Ratiometric fluorescent pH-sensitive polymers for high-throughput monitoring of extracellular pH," RSC Adv., 2016, 6, 46134. Published on May 1, 2016 (Year: 2016).*
Zou, X. et al. "Luminescence materials for pH and oxygen sensing in microbial cells—structures, optical properties, and biological applications," Critical Reviews in Biotechnology, 37:6, 723-738. Sep. 15, 2016 (Year: 2016).*
Georgiev et al., "Synthesis, chemosensing properties and logic behaviour of a novel ratiometric 1, 8-naphthalimide probe based on ICT and PET", Dyes and Pigments, vol. 131, Aug. 2016, available at: https://www.sciencedirect.com/science/article/pii/S0143720816301176?via%Dihub>.

(Continued)

*Primary Examiner* — Christopher Adam Hixson
*Assistant Examiner* — Michelle Adams
(74) *Attorney, Agent, or Firm* — Byrne Poh LLP; Nina R. Horan

(57) ABSTRACT

Fluorescent pH sensors are provided. The fluorescent pH sensor comprises a copolymer for sensing pH and a polymerized form of N-(2-hydroxypropyl)methacrylamide (HPMA) or 2-hydroxyethyl methacrylate (HEMA). The probe for sensing pH has formula (I):

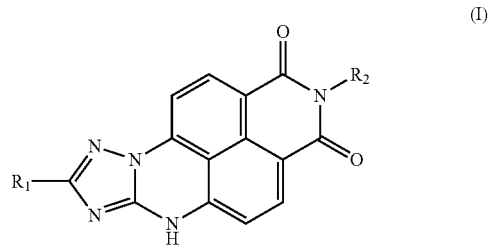

wherein $R_1$ and $R_2$ are as defined herein. The fluorescent pH sensors may be used in determining the pH of a sample and detecting extracellular pH in a sample. Methods for preparing the fluorescent pH sensors and the probe for sensing pH are also provided.

17 Claims, 12 Drawing Sheets

(56) References Cited

OTHER PUBLICATIONS

Hou et al., "Protease-Activated Ratiometric Fluorescent Probe for pH Mapping of Malignant Tumors", ACS Nano, vol. 9, No. 3, Feb. 11, 2015, pp. 3199-3205.
Internation Search Report and Written Opinion dated Mar. 26, 2018 in International Patent Application No. PCT/US2018/014519.
International Preliminary Report on Patentability dated Aug. 1, 2019 in International Patent Application No. PCT/US2018/014519.
Su et al., "Multifunctional PHPMA-derived Polymer for Ratiometric pH Sensing, Fluorescence Imaging, and Magnetic Resonance Imaging", ACS Applied Materials & Interfaces, vol. 10, Iss. 2, Dec. 6, 2017.
Arroyo-Lopez, F. N. et al., "Effects of temperature, pH and sugar concentration on the growth parameters of *Saccharomyces cerevisiae*, S. kudriavzevii and their interspecific hybrid", in International Journal of Food Microbiology, vol. 131, May 31, 2009, pp. 120-127.
Erfle, J. D. et al., "Effect of pH on Fermentation Characteristics and Protein Degradation by Rumen Microorganisms In Vitro", in Journal of Dairy Science, vol. 65, Aug. 1982, pp. 1457-1464.
Kelsch, A. et al., "HPMA Copolymers as Surfactants in the Preparation of Biocompatible Nanoparticles for Biomedical Application", in Biomacromolecules, vol. 13, Nov. 26, 2012, pp. 4179-4187.
Kim, S. H. et al., "Differences in Optimal pH and Temperature for Cell Growth and Antibody Production Between Two Chinese Hamster Ovary Clones Derived from the Same Parental Clone", in Journal of Microbiology and Biotechnology, vol. 17, issue 5, May 31, 2007, pp. 712-720.
Lammers, T. et al. "HPMA copolymers: 30 years of advances", in Advanced Drug Delivery Reviews, vol. 62, Feb. 17, 2010, pp. 119-121.
Lardner, A., "The effects of extracellular pH on immune function", in Journal of Leukocyte Biology, vol. 69, Apr. 1, 2001, pp. 522-530.
Lidstrom, M. et al., "Life-on-a-chip", in Nature Reviews Microbiology, vol. 1, Nov. 1, 2003, pp. 158-164.
Lin, Y. et al., "Factors affecting ethanol fermentation using *Saccharomyces cerevisiae* BY4742", in Biomass and Bioenergy, vol. 47, Dec. 2012, pp. 395-401.
Liu, J. et al., "Glucose metabolic flux distribution of Lactobacillus amylophilus during lactic acid production using kitchen waste saccharified solution", in Microbial Biotechnology, vol. 6, Mar. 14, 2013, pp. 685-693.
Lu, H. et al., "New ratiometric optical oxygen and pH dual sensors with three emission colors for measuring photosynthetic activity in cyanobacteria", in Journal of Materials Chemistry, vol. 21, Nov. 3, 2011, pp. 19293-19301.
Lu, H. et al., "Using fluorine-containing amphiphilic random copolymers to manipulate the quantum yields of aggregation-induced emission fluorophores in aqueous solutions and the use of these polymers for fluorescent bioimaging", in Journal of Materials Chemistry, vol. 22, Mar. 14, 2012, pp. 9890-9900.
Piontek, J. et al., "Acidification increases microbial polysaccharide degradation in the ocean", in Biogeosciences, vol. 7, May 19, 2010, pp. 1615-1624.
Teo, A. et al., "Influence of culture pH on proliferation and cardiac differentiation of murine embryonic stem cells", in Biochemical Engineering Journal, vol. 90, Sep. 15, 2014, pp. 8-15.
Tian, Y. et al., "A fluorescent colorimetric pH sensor and the influences of matrices on sensing performances", in Sensors and Actuators B: Chemical, vol. 188, Nov. 2013, pp. 1-10.
Weber, K., et al., "Microorganisms pumping iron: anaerobic microbial iron oxidation and reduction", in Nature Reviews Microbiology, vol. 4, Oct. 1, 2006, pp. 752-764.
Xu, L. et al., "Acidic Extracellular pH Induces Vascular Endothelial Growth Factor (VEGF) in Human Glioblastoma Cells via ERK1/2 MAPK Signaling Pathway", in Journal of Biological Chemistry, vol. 277, Mar. 29, 2012, pp. 11368-19242.
Zhang, L. et al., "A dual sensor for real-time monitoring of glucose and oxygen", in Biomaterials, vol. 34, Dec. 2013, pp. 9779-9788.
Zhang, L. et al., "A polymer-based ratiometric intracellular glucose sensor", in Chemical Communications, vol. 50, May 7, 2014, pp. 6920-6922.

* cited by examiner

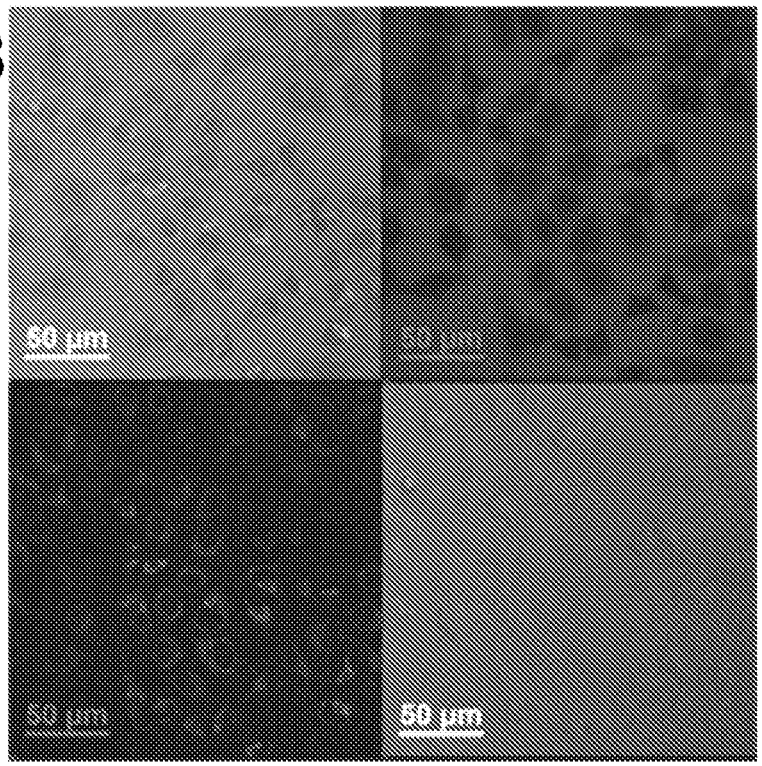
FIG. 1B HeLa
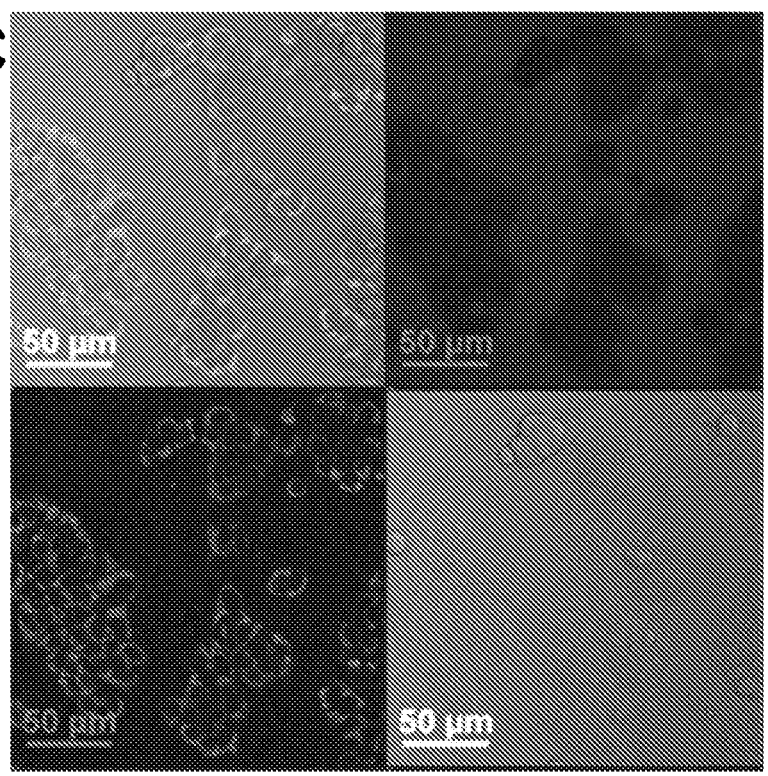
FIG. 1C MCF-7

| pH meter measurement | ps-pH-neutral measurement |
|---|---|
| 6.97 | 6.97 |

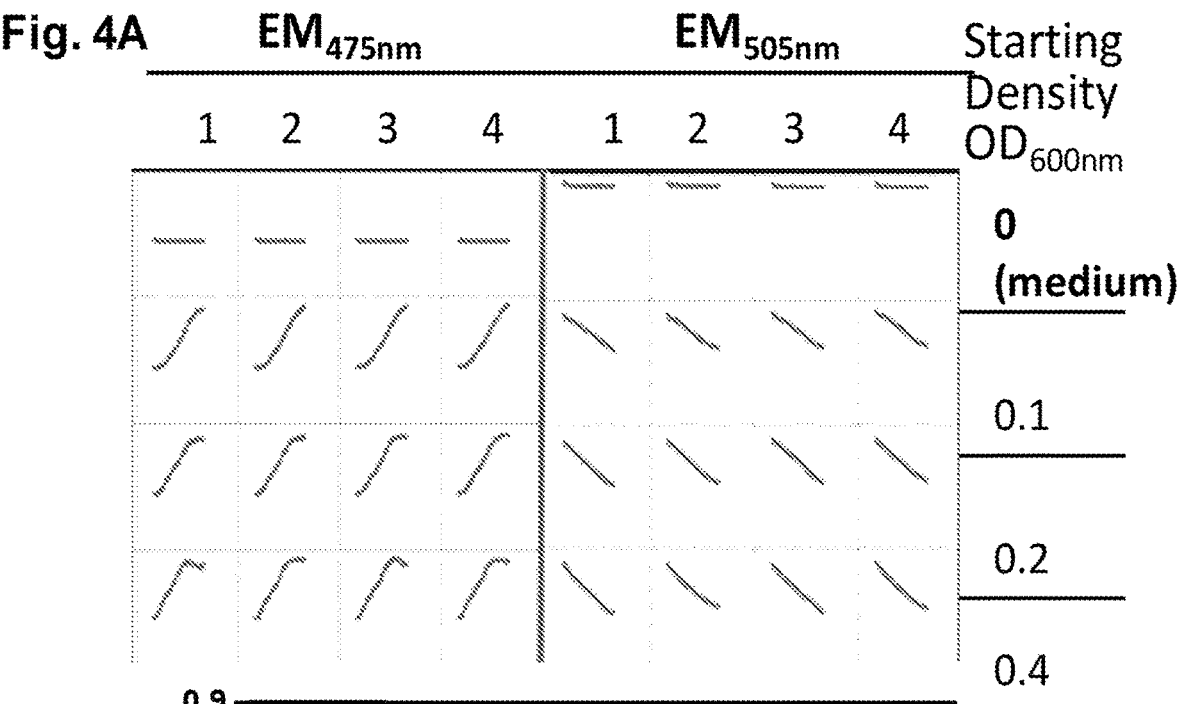
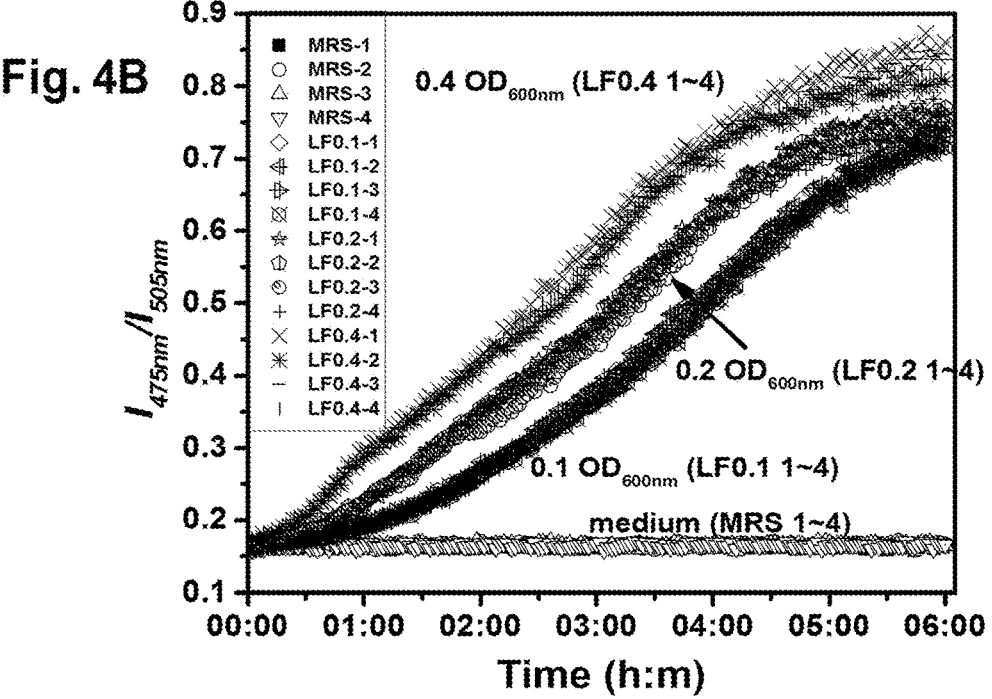

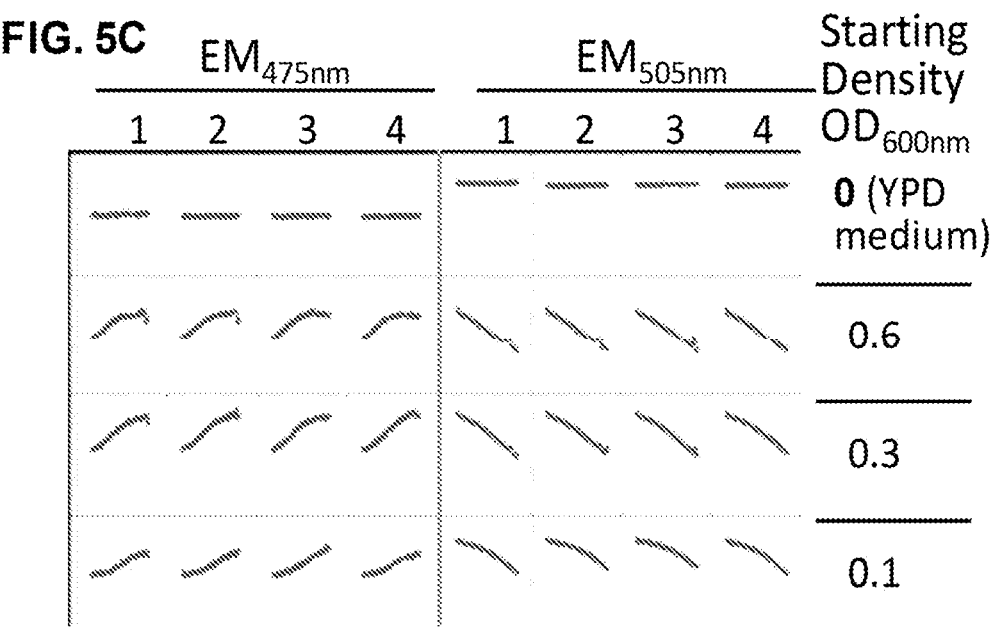
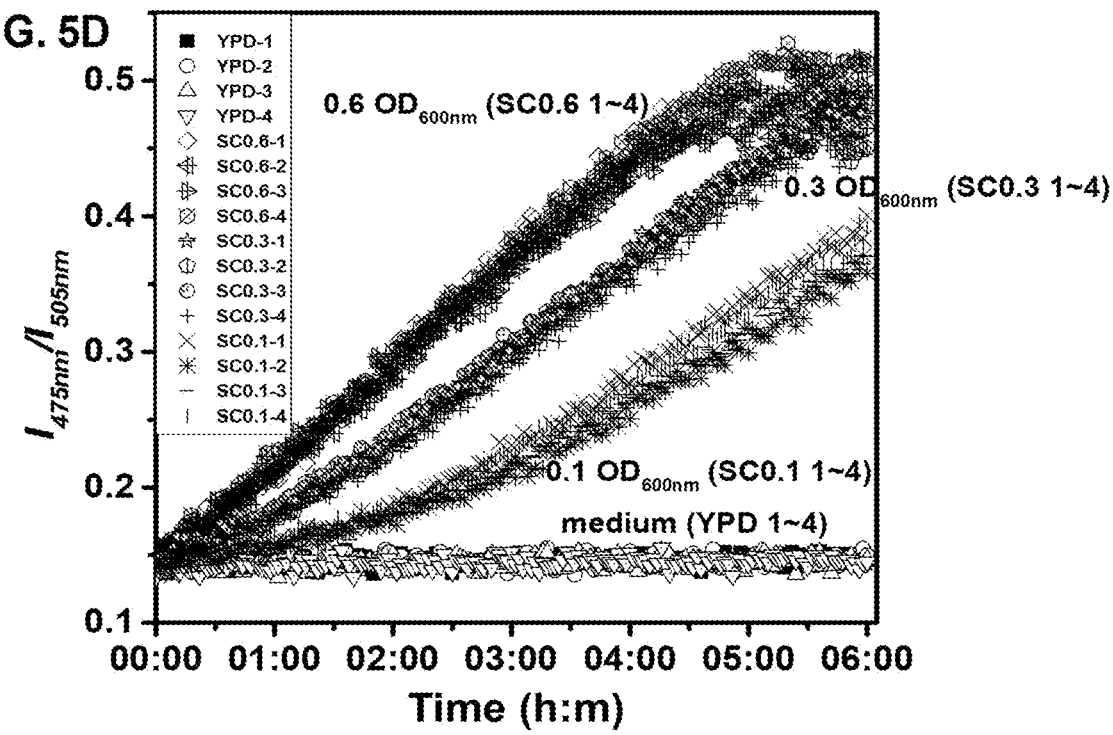

FLUORESCENT PH SENSORS AND METHODS OF PREPARING THEM

FEDERALLY SPONSORED RESEARCH OR DEVELOPMENT

This invention was made with government support under P50 HG002360 and U01 CA164250 awarded by the National Institutes of Health. The government has certain rights in the invention.

BACKGROUND

Although the intracellular pH of microbes and mammalian cells are precisely regulated by homeostasis for the maintenance of metabolism and cell growth, the extracellular pH can vary greatly 1-5. Due to a reprogrammed metabolic pathway and changes of nutrition and oxygen supply, cells commonly exocytose protons or acid metabolites, which results in the acidification of the extracellular microenvironment. Typically, this includes microbes in fermentation and cancer cells[6-10]. Environmental pH has many effects on cells' behaviors. It is well known that an acidic extracellular microenvironment drives tumor cell invasion and metastasis, affects microenvironmental immune function, and influences non-cancerous cell growth and differentiation[11-16]. The extracellular pH of cancer cells is an important parameter that reflects cell growth and responses to treatment. Extracellular pH also affects the growth and production of microbe metabolites. It is a critical parameter in microbial fermentation which needs to be dynamically monitored and well controlled[16-23]. Even though an electrode pH meter can detect the extracellular pH in a large volume, it has shortcomings in analyzing multiple samples with high throughput. A pH sensor with the ability to efficiently and accurately monitor extracellular pH is highly desired for both industry and biomedical research.

Cell metabolism sensors, such as fluorescence pH sensors, are known[24-28]. Because of the high sensitivity, simplicity and the feasibility of miniaturization for microenvironmental detection, fluorescence pH sensors attract significant attention and have been experiencing a series of successes, most of which target the cytosol or some organelles, i.e. mitochondria and lysosomes[28]-[35]. Only a few of them can be specifically limited outside of a cell by either fixing a sensing film on a substrate or anchoring the sensor complex onto the cell surface[27, 28, 36]. There is no doubt that monitoring the pH of the cytosol or specific organelles plays an important role in understanding cellular responses to different stresses. However, detection of pH changes that occur in the extracellular microenvironment of cells is also pivotal to understanding the physiological response of cancer cells during treatment or tumor development[37, 38], as well as to the optimization of microbial metabolism and fermentation[39, 40].

While the sensitivity of fluorescence pH sensors is advantageous, the fluorescence intensity is very easily affected by excitation intensity and the distribution of sensors, which results in a low accuracy of pH measurement. To reduce this negative effect, users must make a standard pH titration curve with the same conditions when they used the sensor to detect the pH. Recently, ratiometric detection has proven be a more accurate method by introducing another emission peak into the sensors[29, 41-45]. Ratiometric sensors normally possess two emission peaks which have different responses to the same pH. The only factor affecting the ratio of emission intensity is pH; neither the local concentration of sensors nor the exciting intensities change the ratios between peaks in a suitable range.

Citation of any reference in this section of the application is not to be construed as an admission that such reference is prior art to the present application.

SUMMARY OF THE INVENTION

The present disclosure relates to fluorescent pH sensor and methods for its preparation and use in determining pH of a sample and detecting extracellular pH in a sample. The present disclosure also relates to methods for preparing a probe for sensing pH.

The fluorescent pH sensor of the present disclosure is water soluble with undetectable cell toxicity. Unlike the small molecular sensing probe, this pH sensor can be exclusively extracellularly localized with the ability to ratiometrically detect pH with high accuracy. By simply mixing and measuring, the fluorescent pH sensor of the present disclosure can be used to perform high-throughput measurements of extracellular pH with a commercial microplate reader.

BRIEF DESCRIPTION OF THE FIGURES

FIGS. 1A-1C show the distribution of pH sensor (ps-pH-neutral) when it is incubated with microbes (FIG. 1A) and mammalian cells (FIGS. 1B and 1C). Cells were not washed in order to show the background emissions and cells were not stained by the polymer. Green emission is from the polymer excited at 488 nm (shown as gray or black), red emission (shown as white; image c in FIGS. 1B and 1C) is from MITOTRACKER® Red (a red dye that stains mitochondria in live cells and its accumulation is dependent upon membrane potential). Image a is an overlay of image b (sensor), image c (MitoTracker) and image d (DPI).

FIG. 2A: Absorbance changes. FIG. 2B: Emission changes excited at 455 nm. FIG. 2C: Ratiometric plots. FIG. 2D: Differences for a few measurements between the results calculated from the fluorescence sensor and those from pH electrodes showing the high accuracy of measuring results using the fluorescent sensor.

FIGS. 4A-4F show the application of ps-pH-neutral in the high throughput detection of bacterial culture with microplates. Bacterial culture containing pH sensors were incubated in microplates at 37° C. The fluorescence intensities at 475 nm and 505 nm of pH sensors were dynamically detected by a microplate reader under 455 nm excitation, A: *L. fermentum*, C: *E. coli*, E: *B. subtilis*. The ratio values ($I_{475\,nm}/I_{505\,nm}$) were calculated and were plotted vs. incubation time, B: *L. fermentum*, D: *E. coli*, F: *B. subtilis*.

FIGS. 5A-5D show the application of ps-pH-neutral in *S. cerevisiae* culture. FIG. 5A, fluorescence spectra of pH sensor were dynamically detected by spectrofluorophotometer under 455 nm excitation. FIG. 5B, growth curve of yeast and pH value which were transferred from data in FIG. 5A were plotted vs. incubation time in a cuvette. FIG. 5C, screen printing data from high throughput analysis of pH in yeast culture with microplate. FIG. 5D, plot curves of ratio values ($I_{475\ nm}/I_{505\ nm}$) from C vs. incubation time.

DETAILED DESCRIPTION OF THE INVENTION

Figure 1A:
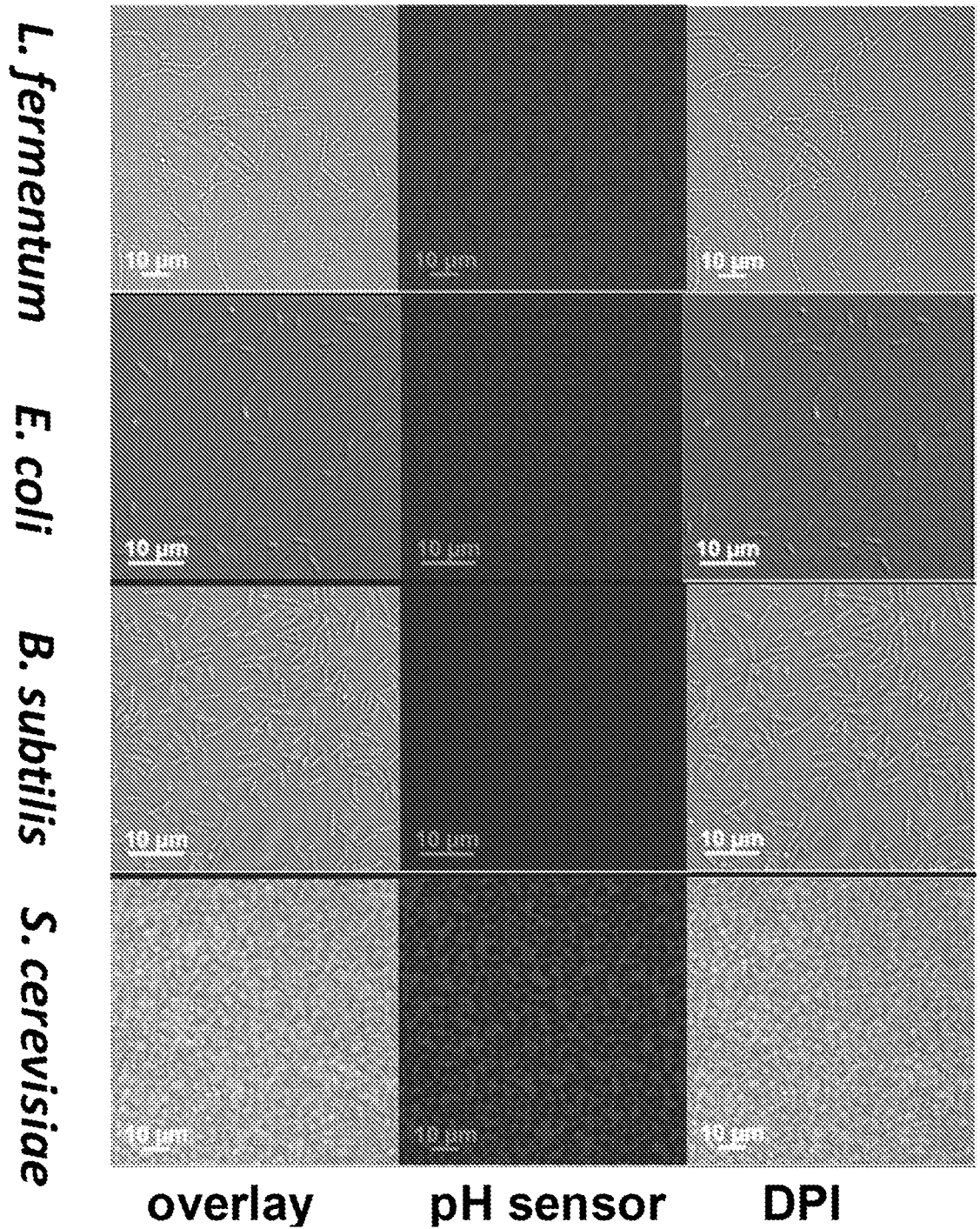

In order that the invention herein described may be fully understood, the following detailed description is set forth.

The invention includes the following:

(1) A fluorescent pH sensor comprising a copolymer, wherein the copolymer comprises:
(a) a polymerized form of a probe for sensing pH; and
(b) a polymerized form of N-(2-hydroxypropyl)methacrylamide (HPMA) or 2-hydroxyethyl methacrylate (HEMA);
wherein:
the probe for sensing pH has formula (I):

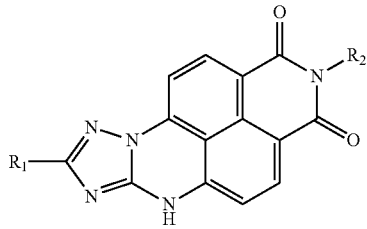

(I)

wherein
$R_1$ is selected from H, ($C_1$-$C_{12}$)haloalkyl, ($C_1$-$C_{12}$) perhaloalkyl, or ($C_1$-$C_{12}$)alkyl, unsubstituted or substituted with one or more substituents selected from the group consisting of NH, N($C_1$-$C_6$)alkyl, OH, O($C_1$-$C_6$)alkyl, SH and S($C_1$-$C_6$)alkyl;
$R_2$ is ($C_mH_{2m}$—X)$_a$—$C_nH_{2n}$—Y;
m is an integer selected from the group consisting of, 1, 2, 3, 4, 5, 6, 7, 8, 9 and 10;
n is an integer selected from the group consisting of 0, 1, 2, 3, 4, 5, 6, 7, 8, 9 and 10;
a is an integer selected from the group consisting of 0, 1, 2, 3, 4, 5, 6, 7, 8, 9 and 10;
X is selected from O, C(=O)O, C(=O)NH, C(=O)N($C_1$-$C_6$)alkyl and O(C=O);
Y is selected from:

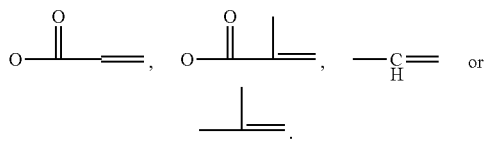

(2) The fluorescent pH sensor of the above (1), further comprising (c) a polymerized form of monomer having a negative charge.
(3) The fluorescent pH sensor of the above (2), wherein the monomer having a negative charge is 2-(methacryloyloxy) ethylsulfonic acid (MESA).
(4) The fluorescent pH sensor of the above (1), further comprising (d) a polymerized form of monomer having a positive charge.

(5) The fluorescent pH sensor of the above (4), wherein the monomer having a positive charge is [2-(methacryloyloxy) ethyl]trimethylammonium chloride (MAETMA).
(6) The fluorescent pH sensor of any of the preceding, wherein, in the probe for sensing pH, $R_1$ is H.
(7) The fluorescent pH sensor of any of the preceding, wherein, in the probe for sensing pH is, $R_2$ is $C_mH_{2m}$—C (=O)O—$C_nH_2$n-Y.
(8) The fluorescent pH sensor of the above (7), wherein m is 5.
(9) The fluorescent pH sensor of the above (7) or (8), wherein n is 2.
(10) The fluorescent pH sensor of any of the preceding, wherein Y is

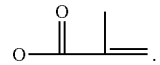

(11) A method for preparing a compound of formula (I),

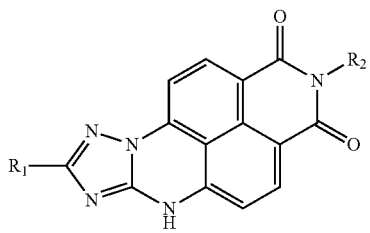

(I)

wherein
$R_1$ is selected from H, ($C_1$-$C_{12}$)haloalkyl, ($C_1$-$C_{12}$) perhaloalkyl, or ($C_1$-$C_{12}$)alkyl, unsubstituted or substituted with one or more substituents selected from the group consisting of NH, N($C_1$-$C_6$)alkyl, OH, O($C_1$-$C_6$)alkyl, SH and S($C_1$-$C_6$)alkyl; $R_2$ is ($C_mH_{2m}$—X)$_a$—$C_nH_{2n}$—Y;
m is an integer selected from the group consisting of 1, 2, 3, 4, 5, 6, 7, 8, 9 and 10;
n is an integer selected from the group consisting of 0, 1, 2, 3, 4, 5, 6, 7, 8, 9 and 10;
a is an integer selected from the group consisting of 0, 1, 2, 3, 4, 5, 6, 7, 8, 9 and 10;
X is selected from O, C(=O)O, C(=O)NH, C(=O) N($C_1$-$C_6$)alkyl and O(C=O);
Y is selected from:

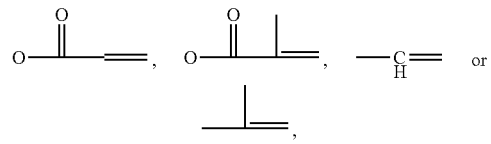

the method comprising
reacting a compound of formula (II) with a monomer selected from 2-hydroxyethyl acrylate or (hydroxyethyl) methacrylate (HEMA), wherein the compound of formula (II) has the formula:

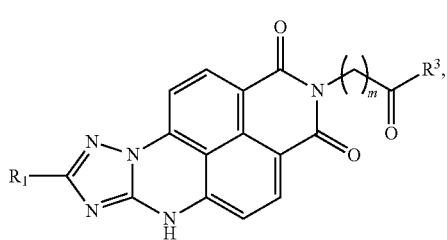

(II)

wherein:
R$_1$ is selected from H, (C$_1$-C$_{12}$)haloalkyl, (C$_1$-C$_{12}$) perhaloalkyl, or (C$_1$-C$_{12}$)alkyl, unsubstituted or substituted with one or more substituents selected from the group consisting of NH, N(C$_1$-C$_6$)alkyl, OH, O(C$_1$-C$_6$)alkyl, SH and S(C$_1$-C$_6$)alkyl;

m is an integer selected from the group consisting of 1, 2, 3, 4, 5, 6, 7, 8, 9 and 10; and R$^3$ is OH, OR$^4$ or halo; and R$^4$ is (C$_1$-C$_6$)alkyl, unsubstituted (C$_6$-C$_{10}$)aryl or substituted (C$_6$-C$_{10}$)aryl.

(12) The method of the above (11), wherein the reacting step comprises reacting the compound of formula (I) with the monomer in the presence of a dehydrating agent.

(13) The method of the above (12), wherein the dehydrating agent is selected from EDC, DCC and CDI.

(14) A method of preparing fluorescent pH sensor, wherein the method comprises the step of:
(a) copolymerizing a probe for sensing pH and a host polymer in the presence of an initiator;
wherein the probe for sensing pH has formula (I):

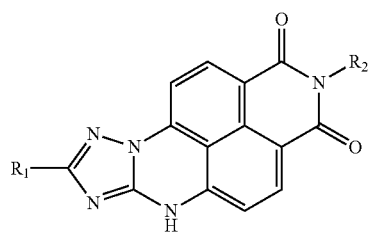

(I)

wherein
R$_1$ is selected from H, (C$_1$-C$_{12}$)haloalkyl, (C$_1$-C$_{12}$) perhaloalkyl, or (C$_1$-C$_{12}$)alkyl, unsubstituted or substituted with one or more substituents selected from the group consisting of NH, N(C$_1$-C$_6$)alkyl, OH, O(C$_1$-C$_6$)alkyl, SH and S(C$_1$-C$_6$)alkyl;

R$_2$ is (C$_m$H$_{2m}$—X)$_a$—C$_n$H$_2$n-Y, m is an integer selected from the group consisting of 1, 2, 3, 4, 5, 6, 7, 8, 9 and 10;

n is an integer selected from the group consisting of 0, 1, 2, 3, 4, 5, 6, 7, 8, 9 and 10;

a is an integer selected from the group consisting of 0, 1, 2, 3, 4, 5, 6, 7, 8, 9 and 10;

X is selected from O, C(=O)O, C(=O)NH, C(=O) N(C$_1$-C$_6$)alkyl and O(C=O);

Y is selected from:

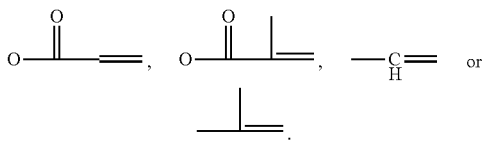

(15) The method of the above (14), wherein the host polymer is HPMA.

(16) The method of the above (14) or (15), wherein the initiator is a thermal initiator.

(17) The method of the above (16), wherein the thermal initiator is AIBN.

(18) The method of any one of the above (14)-(17), wherein the copolymerizing step further comprises co-polymerizing with a monomer having a negative charge.

(19) The method of the above (18), wherein the monomer having a negative charge is MESA.

(20) The method of any one of the above (14)-(17), wherein the copolymerizing step further comprises co-polymerizing with a monomer having a positive charge.

(21) The method of the above (20), wherein the monomer having a positive charge is MAETMA.

(22) A method of determining pH of a sample, wherein the method comprises:
(a) exposing the sample to a fluorescent pH sensor according to any one of the above (1)-(10);
(b) irradiating the sensor at a first wavelength to produce a first emission signal at a second wavelength and a second emission signal at a third wavelength;
(c) determining a first emission intensity at the second wavelength;
(d) determining a second emission intensity at the third wavelength; and
(e) ratiometrically determining the pH of the sample from the first emission intensity and the second emission intensity.

(23) A method of detecting extracellular pH in a sample comprising cells, wherein the method comprises:
(a) exposing the sample to a fluorescent pH sensor according to any one of the above (1)-(10);
(b) irradiating the sensor at a first wavelength to produce a first emission signal at a second wavelength and a second emission signal at a third wavelength;
(c) determining a first emission intensity at the second wavelength;
(d) determining a second emission intensity at the third wavelength; and
(e) ratiometrically determining the pH of the sample from the first emission intensity and the second emission intensity.

(24) The method of the above (22) or (23), wherein the sample is obtained from a cell culture or a subject.

(25) The method of the above (24), wherein the sample comprises a microorganism.

(26) The method of the above (25), wherein the microorganism is bacteria or yeast.

(27) The method of the above (26), wherein the microorganism is selected from the group consisting of *L. fermentum, E. coli*, and *B. substilis*.

(28) The method of the above (26), wherein the microorganism is *S. cerevisiae* (29) The method of the above (24), wherein the cell culture is a mammalian cell culture.

(30) The method of the above (29), wherein the mammalian cell culture is adherent cell lines or suspension cell lines.
(31) The method of the above (30), wherein the mammalian cell culture is selected from HeLa cells and MCF-7 cells.
(32) The method of the above (30), wherein the mammalian cell culture is J774 cells.
(33) The method of any one of the above (22)-(32), wherein more than one sample is used.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The terms "ratiometric method" and "ratiometrically determining" are used interchangeably and are based on the measurement of two probes simultaneously, one that is sensitive to the analyte of interest, and a second that is not, and then taking the ratio of the two [Schaeferling, M., Duerkop, A., 2008. Springer Series on Fluorescence. 5, Springer. 373-414; Xu, H. et al., 2001, Anal. Chem. 73, 4124-4133; Kermis, H. R., et al., 2008. Sens. Actuators B, 128, 388-398.]. The ratiometric method has been known to increase measurement accuracy and to alleviate environmental influences, such as fluctuations in excitation source intensity, variance in probe concentration, and uncontrollable variations in background fluorescence.

The terms "pH sensor," "pH probe" and "probe for sensing pH" are used interchangeably and may be abbreviated as "pHS".

The term "internal reference probe" may be abbreviated as "IRP".

The term "polymerized form of a probe" refers to a monomer unit of a probe that is capable of undergoing a polymerization reaction to produce a polymer of the probe or a co-polymer with one or more types of probes or matrices. In a first embodiment, the co-polymer comprises a probe for sensing pH and an internal reference probe. In a second embodiment, the co-polymer may further comprise a matrix.

The term "polymerized probe" refers to the polymer product of a probe.

The term "halo" refers to F, Cl, Br, and I.

The term "$(C_1-C_{12})$alkyl" refers to saturated linear and branched hydrocarbon structures having 1, 2, 3, 4, 5, 6, 7, 8, 9, 10, 11 or 12 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_{12})$alkyl groups include methyl, ethyl, n-propyl, iso-propyl, n-butyl, tert-butyl, n-hexyl, 2-methylpentyl, 3-methylpentyl, 2,2-dimethylbutyl, 2,3-dimethylbutyl, n-heptyl, 2-methylhexyl, 2,2-dimethylpentyl, 3-ethylpentyl, 2,2,3-trimethylbutyl, n-octyl, 2-methyl, hexane, 2,2-dimethylpentyl, 3-ethylpentyl, 2,2,3-trimethylbutyl, n-nonyl, 2-methyloctyl, 2,2-dimethylheptyl, 3-ethylheptyl, 2,2,3-trimethylhexyl, 3-ethyl-2-methylhexyl, 2,2,3,3-treatmethylpentyl, 3-ethyl-2,2-dimethylpentyl, 3,3-diethylpentyl, n-decyl, 2-methylnonyl, 3-methylnonyl, 4-methylnonyl, 5-methylnonyl, 3-ethyloctyl, 4-ethyloctyl, 2,2-dimethyloctyl, 3,5-dimethyloctyl, 4,4-dimethyloctyl, 4,5-dimethyloctyl, 3-ethyl-2-methylheptyl, 2,2,3-trimethylheptyl, 2-methyl-3-(1-methylethyl)hexyl, 3,3-diethylhexyl, 3-ethyl, 2,2-dimethylhexyl, 2,2,3,3-tetramethylhexyl, 2,4-dimethyl-3-(1-methylethyl)pentyl, 3,3-diethyl-2-methylpentyl, 3-ethyl-2,2,3-trimethylpentyl, 2,2,3,3,4-pentamethylpentyl, n-undecyl, 2-methyldecyl, 3-ethylnonyl, 2,2-dimethylnonyl, 4-propyloctyl, 3-ethyl-2-methyloctyl, 2,2,3-trimethyloctyl, 3,3-diethylheptyl, 3-ethyl-2,2-dimethylheptyl, 2,2,3,3-tetramethylheptyl, 2-methyl-4-propylheptyl, 4-(1,1-dimethylethyl)heptyl, 2,2,3,3,4-pentamethylhexyl, 3-ethyl-2,2,3-trimethylhexyl, 3,3-diethyl-2-methylhexyl, 2,2-dimethyl-3-(1-methylethyl) hexyl, 2,2,3,3,4,4-hexamethylpentyl, 3-ethyl-2,2,3,4-tetramethylpentyl; 3,3-diethyl-2,2-dimethylpentyl, 3,3-diethyl-2,2-dimethylpentyl, 2,2,3-trimethyl-3-(1-methylethyl)pentyl, n-dodecyl, 2-methylundecyl, 2,2-dimethyldecyl, 3-ethyldecyl, 2,2,3-trimethylnonyl, 3-ethyl-2-methylnonyl, 4-propylnonyl, 2,2,3,3-tetramethyloctyl, 3-ethyl-2,2-dimethyloctyl, 3,3-diethyloctyl, 2-methyl-4-propyloctyl, 4-(1,1-dimethylethyl)octyl, 2,2,3,3,4-pentamethylheptyl, 3-ethyl-2,2,3-trimethylheptyl, 3,3-diethyl-2-methylheptyl, 2,2-dimethyl-4-propylheptyl, 3-ethyl-4-propylheptyl, 4-(1,1-dimethylethyl)-2-methylheptyl, 2,2,3,3,4,4-hexamethylhexyl, 3-ethyl-2,2,3,4-tetramethylhexyl, 3,3-diethyl-2,2-dimethylhexyl, 3,3,4-triethylhexyl, 2,2,3-trimethyl-3-(1-methylethyl)hexyl, 3-ethyl-2-methyl-3-(1-methylethyl)hexyl, 3-(1,1-dimethylethyl)-2,2-dimethylhexyl, 3-ethyl-2,2,3,4,4-pentamethylpentyl, 3,3-diethyl-2,2,4-trimethylpentyl, 2,2,3,4-tetramethyl-3-(1-methylethyl)pentyl, 3-ethyl-2,4-dimethyl-3-(1-methylethyl)pentyl and the like.

The term "$(C_1-C_6)$alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-hexyl, and the like.

The term "$(C_{1-12})$perhaloalkyl" refers to a $(C_1-C_{12})$alkyl group wherein every hydrogen atom is replaced by halo, each halo being independently selected. Examples of $(C_1-C_{12})$perhaloalkyl groups include —$CF_3$, —$CCl_3$, —$CF_2CF_3$, —$CCl_2CF_3$, —$CClFCClF_2$, —$CF(CF_3)_2$, —$CBr(CF_3)(CFCl_2)$, —$(CF_2)_4CF_3$, —$(CF_2)_5CF_3$, —$(CF_2)_6CF_3$, —$(CF_2)_7CF_3$, —$(CF_2)_8CF_3$, —$(CF_2)_9CF_3$, —$(CF_2)_{10}CF_3$, —$(CF_2)_{11}CF_3$ and the like.

The term "$(C_{1-12})$haloalkyl" refers to a $(C_{1-12})$alkyl group wherein at least one hydrogen atom is replaced by halo but wherein the $(C_{1-12})$haloalkyl contains fewer halos than a $(C_1—Cl_2)$perhaloalkyl having the same number of carbon atoms as the $(C_{1-12})$haloalkyl. Each halo of a $(C_1$-$C_{12})$ haloalkyl is independently selected. Examples of $(C_1$-$C_{12})$ haloalkyl groups include —CHF$_2$, —CH$_2$F, —CHFCl, —CH$_2$CF$_3$, —CHClCHF$_2$, —CHFCHClF, —CH(CF$_3$)$_2$, —CH(CF$_3$)(CH$_3$), —CBr(CHF$_2$)(CHCl$_2$), —(CH$_2$)$_4$CH$_2$F, —(CH$_2$)$_4$CF$_3$, —(CH$_2$)$_5$CH$_2$F, —(CH$_2$)$_5$CF$_3$, —(CH$_2$)$_6$CH$_2$F, —(CH$_2$)$_6$CF$_3$, —(CH$_2$)$_7$CH$_2$F, —(CH$_2$)$_7$CF$_3$, —(CH$_2$)$_8$CH$_2$F, —(CH$_2$)$_8$CF$_3$, —(CH$_2$)$_9$CH$_2$F, —(CH$_2$)$_9$CF$_3$, —(CH$_2$)$_{10}$CH$_2$F, —(CH$_2$)$_{10}$CF$_3$, —(CH$_2$)$_{11}$CH$_2$F, —(CH$_2$)$_{11}$CF$_3$ and the like.

The term "$(C_6$-$C_{10})$aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of $(C_6$-$C_{10})$aryl groups include without limitation phenyl, naphthyl, indanyl, indenyl and tetralinyl. In some embodiments, the aryl is phenyl.

The term "initiator" refers to a compound that generates a free radical.

The term "thermal initiator" refers to a compound that generates a free radical at an elevated temperature. Suitable thermal initiators that can be used include, but are not limited to AIBN and BPO.

The term "photoinitiator" refers to a compound that generates a free radical when exposed to light. Suitable photo-initiators that can be used include, but are not limited to, IRACURE® 819, 4-phenyl benzophenone, methyl o-benzoyl benzoate and benzyl dimethyl ketal. In some aspects, the photo-initiator is IRACURE® 819.

The term "dehydrating agent" refers to a compound that reacts with water in a chemical reaction. Dehydrating agents are known in the art and include, but are not limited to, EDC, DCC or CDI.

The abbreviation "AIBN" refers to 2,2'-azobis(2-methyl-propionitrile).

Sensor Design

The present disclosure provides a fluorescent pH sensor that is water soluble with undetectable cell toxicity. In particular, the fluorescent pH sensor comprises a copolymer, wherein the copolymer comprises: (a) a polymerized form of a probe for sensing pH; and (b) a polymerized form of N-(2-hydroxypropyl)methacrylamide (HPMA) or 2-hydroxyethyl methacrylate (HEMA).

The probe for sensing pH has formula (I):

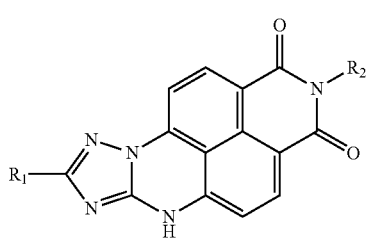

(I)

wherein
$R_1$ is selected from H, $(C_1$-$C_{12})$haloalkyl, $(C_1$-$C_{12})$perhaloalkyl, or $(C_1$-$C_{12})$alkyl, unsubstituted or substituted with one or more substituents selected from the group consisting of NH, N$(C_1$-$C_6)$alkyl, OH, O$(C_1$-$C_6)$alkyl, SH and S$(C_1$-$C_6)$alkyl;
$R_2$ is $(C_mH_{2m}$—X$)_a$—$C_nH_{2n}$—Y;
m is an integer selected from the group consisting of, 1, 2, 3, 4, 5, 6, 7, 8, 9 and 10;
n is an integer selected from the group consisting of 0, 1, 2, 3, 4, 5, 6, 7, 8, 9 and 10;
a is an integer selected from the group consisting of 0, 1, 2, 3, 4, 5, 6, 7, 8, 9 and 10;
X is selected from O, C(=O)O, C(=O)NH, C(=O)N$(C_1$-$C_6)$alkyl and O(C=O);
Y is selected from:

In some embodiments, $R_1$ is H, $(C_1$-$C_{12})$haloalkyl, or $(C_1$-$C_{12})$perhaloalkyl. In some embodiments, $R_1$ is H, $(C_1$-$C_{12})$haloalkyl, or $(C_1$-$C_{12})$alkyl. In some embodiments, $R_1$ is H, $(C_1$-$C_{12})$perhaloalkyl, or $(C_1$-$C_{12})$alkyl. In some embodiments, $R_1$ is $(C_1$-$C_{12})$haloalkyl, $(C_1$-$C_{12})$perhaloalkyl, or $(C_1$-$C_{12})$alkyl. In some embodiments, $R_1$ is H or $(C_1$-$C_{12})$haloalkyl. In some embodiments, $R_1$ is H or $(C_1$-$C_{12})$perhaloalkyl. In some embodiments, $R_1$ is H or $(C_1$-$C_{12})$alkyl. In some embodiments, $R_1$ is H. In some embodiments, $R_1$ is $(C_1$-$C_{12})$haloalkyl. In some embodiments, $R_1$ is $(C_1$-$C_{12})$perhaloalkyl. In some embodiments, $R_1$ $(C_1$-$C_{12})$alkyl.

In some embodiments, X is O, C(=O)O, C(=O)NH, or C(=O)N$(C_1$-$C_6)$alkyl. In some embodiments, X is O, C(=O)O, C(=O)NH, or O(C=O). In some embodiments, X is C(=O)O, C(=O)NH, C(=O)N$(C_1$-$C_6)$alkyl or O(C=O). In some embodiments, X is C(=O)O, C(=O)NH, C(=O)N$(C_1$-$C_6)$alkyl or O(C=O). In some embodiments, X is O or C(=O)O. In some embodiments, X is O or C(=O)NH. In some embodiments, X is O, or C(=O)N$(C_1$-$C_6)$alkyl. In some embodiments, X is O or O(C=O). In some embodiments, X is C(=O)O or C(=O)NH. In some embodiments, X is (=O)O or C(=O)N$(C_1$-$C_6)$alkyl. In some embodiments, X is C(=O)O or O(C=O). In some embodiments, X is C(=O)NH or C(=O)N$(C_1$-$C_6)$alkyl. In some embodiments, X is C(=O)NH or O(C=O). In some embodiments, X is O. In some embodiments, X is C(=O)O. In some embodiments, X is C(=O)NH. In some embodiments, X is C(=O)N$(C_1$-$C_6)$alkyl. In some embodiments, X is O(C=O).

In some embodiments, $R_2$ is $C_mH_{2m}$—C(=O)O—$C_nH_{2n}$—Y. In some embodiments, $R_2$ is $(C_mH_{2m}$—C(=O)NH—$C_nH_{2n}$—Y. In some embodiments, $R_2$ is $(C_mH_{2m}$—C(=O)N$(C_1$-$C_6)$alkyl-$C_nH_{2n}$—Y. In some embodiments, $R_2$ is $(C_mH_{2m}$—O(C=O)—$C_nH_{2n}$—Y.

In some embodiments, m is an integer selected from the group consisting of, 1, 2, 3, 4, 5, 6, 7, 8, 9 and 10. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10.

In some embodiments, n is an integer selected from the group consisting of 0, 1, 2, 3, 4, 5, 6, 7, 8, 9 and 10. In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, a is an integer selected from the group consisting of 0, 1, 2, 3, 4, 5, 6, 7, 8, 9 and 10. In some embodiments, a is 0. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10.

In some embodiments, Y is

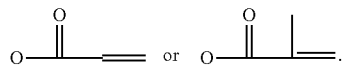

In some embodiments, Y is

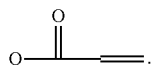

In some embodiments, Y is

In some embodiments, the fluorescent pH sensor as described herein further comprises (c) a polymerized form of monomer having a negative charge. In some aspects of this embodiment, the monomer having a negative charge is 2-(methacryloyloxy)ethylsulfonic acid (MESA).

In some embodiments, the fluorescent pH sensor as described herein further comprises (d) a polymerized form of monomer having a positive charge. In some aspects of this embodiment, the monomer having a positive charge is [2-(methacryloyloxy)ethyl]trimethylammonium chloride (MAETMA).

In some embodiments, fluorescent pH sensor comprises a polymerized form of N-(2-hydroxypropyl)methacrylamide (HPMA). In some embodiments, fluorescent pH sensor comprises a polymerized form of 2-hydroxyethyl methacrylate (HEMA).

Methods of Preparing a Compound of Formula (I)

The present disclosure provides a method for preparing a compound of formula (I),

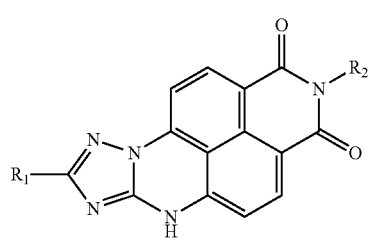

wherein
$R_1$ is selected from H, $(C_1-C_{12})$haloalkyl, $(C_1-C_{12})$perhaloalkyl, or $(C_1-C_{12})$alkyl, unsubstituted or substituted with one or more substituents selected from the group consisting of NH, $N(C_1-C_6)$alkyl, OH, $O(C_1-C_6)$alkyl, SH and $S(C_1-C_6)$alkyl; $R_2$ is $(C_mH_{2m}-X)_a-C_nH_{2n}-Y$;
m is an integer selected from the group consisting of 1, 2, 3, 4, 5, 6, 7, 8, 9 and 10;

n is an integer selected from the group consisting of 0, 1, 2, 3, 4, 5, 6, 7, 8, 9 and 10;
a is an integer selected from the group consisting of 0, 1, 2, 3, 4, 5, 6, 7, 8, 9 and 10;
X is selected from O, C(=O)O, C(=O)NH, C(=O)N($C_1-C_6$)alkyl and O(C=O);
Y is selected from:

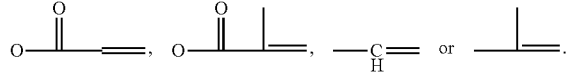

The method comprises reacting a compound of formula (II) with a monomer selected from 2-hydroxyethyl acrylate or (hydroxyethyl)methacrylate (HEMA).

The compound of formula (II) used in this method has the formula:

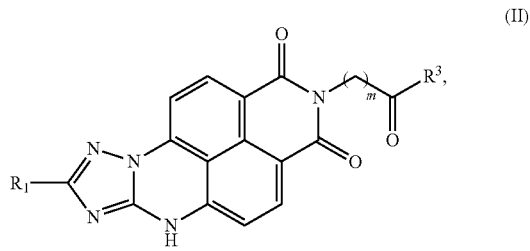

wherein:
$R_1$ is selected from H, $(C_1-C_{12})$haloalkyl, $(C_1-C_{12})$perhaloalkyl, or $(C_1-C_{12})$alkyl, unsubstituted or substituted with one or more substituents selected from the group consisting of NH, $N(C_1-C_6)$alkyl, OH, $O(C_1-C_6)$alkyl, SH and $S(C_1-C_6)$alkyl;
m is an integer selected from the group consisting of 1, 2, 3, 4, 5, 6, 7, 8, 9 and 10; and
$R^3$ is OH, $OR^4$ or halo; and
$R^4$ is $(C_1-C_6)$alkyl, unsubstituted $(C_6-C_{10})$aryl or substituted $(C_6-C_{10})$aryl.

In some embodiments, the reacting step comprises reacting the compound of formula (I) with the monomer in the presence of a dehydrating agent. In some embodiments, the dehydrating agent is selected from EDC, DCC and CDI.

Methods of Preparing the Sensors

The present disclosure provides a method of preparing a fluorescent pH sensor as described herein. The method comprises the step of: (a) copolymerizing a probe for sensing pH and a host polymer in the presence of an initiator. The probe for sensing pH has formula (I) as described herein.

In some embodiments, the host polymer is HPMA.

In some embodiments, the initiator is a thermal initiator. In some aspects of this embodiment, the thermal initiator is AIBN.

In some embodiments, the copolymerizing step further comprises co-polymerizing with a monomer having a negative charge. In some aspects of this embodiment, the monomer having a negative charge is MESA.

In some embodiments, the copolymerizing step further comprises co-polymerizing with a monomer having a positive charge. In some aspects of this embodiment, the monomer having a positive charge is MAETMA.

Methods of Using the Sensors

The present disclosure provides a method of determining pH of a sample. The method comprises exposing the sample to a fluorescent pH sensor. The fluorescent pH sensor can be any of the sensors described herein.

The sensor is then irradiated at a first wavelength to produce a first emission signal at a second wavelength and a second emission signal at a third wavelength. The first emission intensity at the second wavelength and the second emission intensity at the third wavelength are determined. The pH of the sample is then determined ratiometrically from the first emission intensity and the second emission intensity.

The present disclosure also provides a method of detecting extracellular pH in a sample comprising cells. The method comprises exposing the sample to a fluorescent pH sensor. The fluorescent pH sensor can be any of the sensors described herein.

The sensor is then irradiated at a first wavelength to produce a first emission signal at a second wavelength and a second emission signal at a third wavelength. The first emission intensity at the second wavelength and the second emission intensity at the third wavelength are determined. The pH of the sample is then determined ratiometrically from the first emission intensity and the second emission intensity.

In each of the methods described in above, the sample can be obtained from a cell culture or a subject. In some aspects, the sample comprises a microorganism. In some aspects of this embodiment, the microorganism is bacteria or yeast. In some aspects of this embodiment, the microorganism is selected from the group consisting of L. fermentum, E. coli, and B. substilis.

In some aspects of this embodiment, the microorganism is S. cerevisiae.

In some aspects in which the sample is obtained from a cell culture, the cell culture is a mammalian cell culture. In some aspects of this embodiment, the mammalian cell culture is adherent cell lines or suspension cell lines. In some aspects of this embodiment, the mammalian cell culture is selected from HeLa cells and MCF-7 cells. In some aspects of this embodiment, the mammalian cell culture is J774 cells.

In each of the methods described above, more than one sample can be used. Thus, the method can be performed in a high throughput format.

In order that this invention be more fully understood, the following examples are set forth.

These examples are for the purpose of illustration only and are not to be construed as limiting the scope of the invention in any way.

EXAMPLES

Materials and Reagents

All chemicals and reaction solvents were of analytical grade and were used without further purification. N-(2-hydroxyethyl)-4-bromine-1,8-naphthalimide, 3-amino-1,2,4-triazole 6-bromohexanoic acid, dichloromethane, methanol, triethylamine, methacryloyl chloride, N,N'-dimethylformamide (DMF), dimethyl sulfoxide (DMSO), -2-propanol, [2-(methacryloyloxy)ethyl]trimethylammonium chloride (MAETMA), 4-dimethylaminopyridine (DMAP), 1-ethyl-3-(3-dimethylaminopropyl)carbodiimide (EDC), and azobisisobutyronitrile (AIBN) were commercially available from Sigma-Aldrich (St. Louis, Mo.) and used without further purification. 2-(Methacryloyloxy)ethylsulfonic acid sodium salt (MAESA) was purchased from Fisher Scientific. N-(2-hydroxypropyl)methacrylamide (HPMA) was synthesized and purified according to a published method[25,50]. The pH sensing probe ANNA, which was named by Zhou J. et al (Scheme 1), was synthesized according to a modified procedure in the literature[41]. Deionized water was used for the preparation of buffer solutions. The pH values were determined with a digital pH meter (Thermo Electron Corporation, Beverly, Mass.) and calibrated at room temperature with standard buffers.

Instruments

A Varian liquid-state NMR operated at 400 MHz for $^1$H NMR was used for NMR spectra measurements. A Shimadzu UV-3600 UV-Vis-NIR spectrophotometer (Shimadzu Scientific Instruments, Columbia, Md.) was used for absorbance measurements. A Shimadzu RF-5301 spectrofluorophotometer was used for fluorescence measurements. Waters Breeze gel filtration chromatography (GPC) was used for polymer molecular weight measurement. SYNERGY™ H4 Hybrid Multi-Mode Microplate Reader (BioTeK) was used for pH measurement with standard 96-well plates. A Beckman DU 530 UV/Vis Spectrophotometer (Beckman Coulter) was used to measure the microbe density ($OD_{600nm}$). A Confocal microscope (Nikon, TE2000E) was used for cell imaging.

Synthesis of the Monomeric of pH Probe (ANNA-HEMA)

Scheme 1. Synthesis of the monomeric pH sensing phobe (ANNA-HEMA)

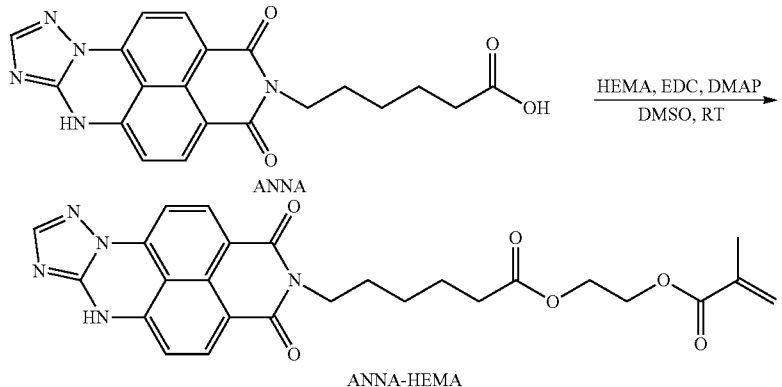

The polymerizable pH probe, ANNA-HEMA, was synthesized according to Scheme 1. 100 mg (0.26 mmol) of ANNA, EDC (121 mg, 0.78 mmol) and DMAP (93.5 mg, 0.78 mmol) were dissolved in 3 mL of DMSO. 102 mg of HEMA (0.78 mmol) was slowly added into the above mixture at room temperature. The reaction was stirred overnight at room temperature. 150 mL of dichloromethane was added to the reaction mixture. The organic phase was washed with ice-cold water twice and one time with brine and then dried over $MgSO_4$. The product of ANNA-HEMA was purified by silica column chromatography with methylene chloride/methanol (95:5 by volume) containing 0.3% triethylamine. Yield: 100 mg (78.1%). $^1$H NMR ($CDCl_3$, ppm, δ): 8.61 (d, 1H), 8.40 (d, 1H), 8.04 (d, 1H), 7.52 (d, 1H), 6.88 (d, 1H), 6.10 (s, 1H), 5.57 (s, 1H), 4.31 (s, 4H), 4.18 (t, 2H), 2.35 (t, 2H), 1.72 (m, 1.76-1.68, 4H), 1.46 (m, 1.50-1.42, 2H). MOLDI-TOF (m/z): 504.19, calcd: $C_{26}H_{25}N_5O_6$, (M+H), 504.18.

Polymerization and Characterization of the pH Sensors (Ps-pH)

250 mg of HPMA, 6.0 mg of ANNA-HEMA, 30 mg of MAETMA or MESA (for ps-pH-positive or ps-pH-negative, respectively), and 5.0 mg AIBN were dissolved in 3 mL of DMF. This solution was degassed three times through a standard freeze-thaw process. The monomers were polymerized at 65° C. for 16 h under nitrogen. The polymer was precipitated into 150 mL of acetone from the DMF solution. The polymer was re-dissolved in 3 mL methanol and re-precipitated into 100 mL of ether. This produced 198 mg of ps-pH-neutral (yield: 77.3%), 190 mg of ps-pH-negative (yield: 66.4%), 176 mg of ps-pH-positive (yield: 61.5%). The sensor's contents in polymers, which were determined by UV absorbance at pH 7.0, are all around 0.02 g per gram of polymers.

Scheme 2. Chemical structures of the monomers used for preparing the sensing polymers and a polymerization scheme.

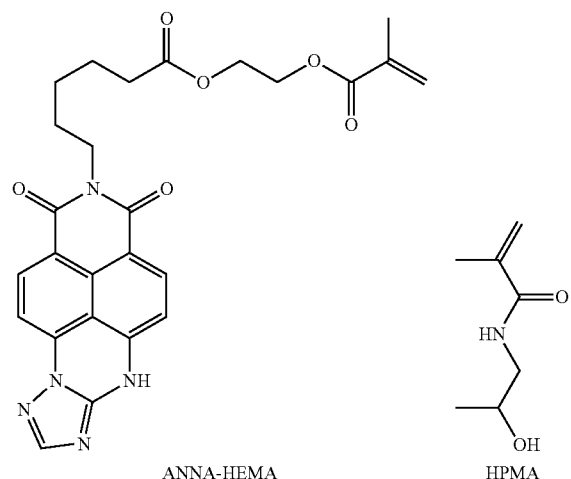

ANNA-HEMA HPMA

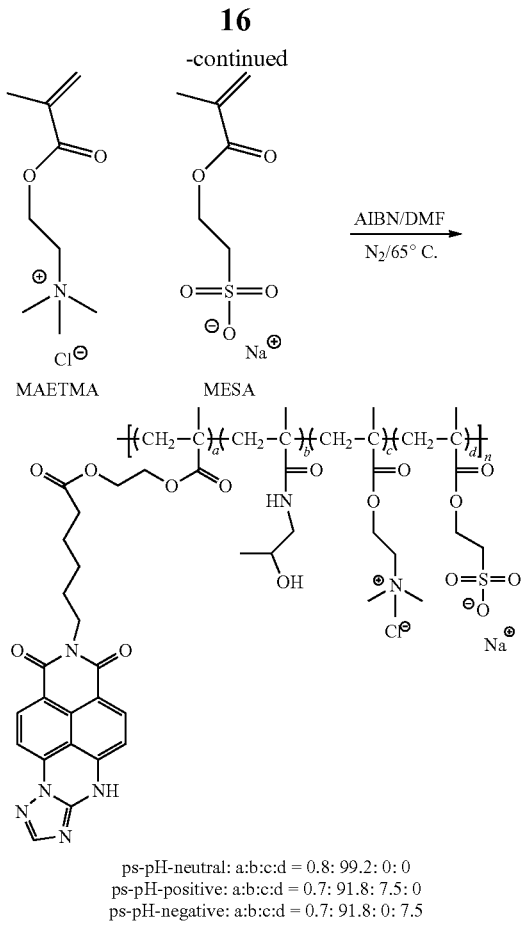

MAETMA  MESA ps-pH-neutral: a:b:c:d = 0.8: 99.2: 0: 0
ps-pH-positive: a:b:c:d = 0.7: 91.8: 7.5: 0
ps-pH-negative: a:b:c:d = 0.7: 91.8: 0: 7.5

Culture of L. fermentum (Lactobacillus fermentum) for Cellular Distribution Assay and Extracellular pH Sensing L. fermentum (ATCC® 9338™) were cultured in lactobacilli de Man-Rogosa-Sharpe (MRS) broth following the culture method provided by the supplier. The concentration of lactobacilli was estimated by measuring the optical density at 600 nm ($OD_{600\ nm}$). According to the amount of cells designated for experiments, an appropriate volume of culture was spun down to harvest cells. The final pellet was re-suspended into fresh MRS medium with or without 10 g/mL of ps-pH sensor to get the required concentration for experiments. Final concentration of the pH probe in the analysis solution is 0.4 μM.

Culture of E. coli (Escherichia coli) and B. subtilis (Bacillus subtilis) for Cellular Distribution Assay and Extracellular pH Sensing E. coli (JM109) or B. subtilis (168) were cultured in Luria-Bertani (LB) broth overnight at 37° C. with vigorous shaking at 180 rpm. The concentrations of bacteria in culture were estimated by measuring the optical density at 600 nm ($OD_{600\ nm}$). Bacteria were harvested from the appropriate volume of culture by spin-down according to the amount of cells expected for experiments. The final pellet was re-suspended into fresh LB medium with or without 10 g/mL of ps-pH sensor to get the required concentration for experiments.

Culture of S. cerevisiae (Saccharomyces cerevisiae) for cellular distribution assay and extracellular pH sensing S. cerevisiae (ATCC® 9763™) were cultured in yeast extract peptone dextrose (YEPD) medium overnight at 30° C. with vigorous shaking at 180 rpm. The culture was diluted with fresh YEPD medium, followed by additional two hours of incubation at 30° C. According to the concentrations of yeast in culture which was estimated by measuring the optical density at 600 nm ($OD_{600\,nm}$), yeast were harvested from the appropriate volume of culture by spin-down. The final pellet was re-suspended into fresh YEPD medium with or without 10 μg/mL of ps-pH sensor to get the required concentration for experiments.

Culture of HeLa Cells and MCF-7 Cells for Cellular Distribution Assay and Extracellular pH Test Both HeLa and MCF-7 cell lines were purchased from ATCC. Cells were seeded in a standard 96-well plate and cultured in Dulbecco's Modified Eagle Medium (DMEM) supplemented with 10% fetal bovine serum (FBS), 1% penicillin/streptomycin and incubated at 37° C. in a 5% $CO_2$ atmosphere. After getting 100% of confluence, each well was washed by PBS once and the fresh DMEM adjusted to different pH (medium-pH) was added to each well, respectively. The Medium-pH containing 10 μg/mL sensors (ps-pH-neutral) and medium only were used as control in the experiment.

Cellular Distribution of pH Sensors Assay by Fluorescent Microscopy

Mammalian cells or microbes were seeded into a 96-well plate and incubated in their medium containing 10 μg/mL pH sensors for 24 h. For mammalian cells (HeLa cell, MCF-7 cell or J774 cell), MITOTRACKER® Red FM (ThermoFisher Scientific) were added into medium and incubated for 4 h before imaging. The localization of pH sensors were detected by co-focal fluorescence microscopy under 488 nm excitation.

Detect the Microbial Growth and pH Change of Culture

Around 0.1 $OD_{600}$ of fresh microbial culture containing 10 μg/mL of pH sensors (ps-pH-neutral) was sealed into a cuvette and incubated in a water bath at an optimal temperature specific to them. After re-suspending cells by up-down shaking, cell density was measured by $OD_{600}$. The spectra of pH sensors in culture were detected by a spectrofluorophotometer under the condition of 455 nm excitation. A pH value was calculated based on ratios of emission intensity at 475 nm ($I_{475}$ nm) to emission intensity at 505 nm ($I_{505\,nm}$).

Detection of the Extracellular pH with a Microplate Reader

Microbes were re-suspended into fresh medium containing 10 μg/mL ps-pH-neutral sensor and aliquot into 96-well plate by 100 μl per well. Medium containing either sensor or microbes only were aliquoted into parallel wells as experimental controls. After sealing wells with mineral oil to prevent oxygen exchange, the emission intensities at 475 nm and 505 nm from each well were immediately monitored by a microplate reader with 455 nm of excitation.

Results and Discussion

Design and Synthesis of Polymeric pH Sensors

The monomer of the pH sensing probe was synthesized according to Scheme 1. Three kinds of polymeric pH sensors carrying different charges were synthesized according to the scheme in Scheme 2. The molar ratio of monomers used in reaction (a:b:c or d) was 0.7:91.8:7.5. We use poly(N-(2-hydroxypropyl)methacrylamide) (PHPMA), which has been widely used as the biocompatible host polymer, to increase the water solubility of sensors[25, 51, 52]. A small fraction of poly[2-(methacryloyloxy)ethyl]trimethylammonium chloride (PMAETMA) or poly [2-(methacryloyloxy)ethyl]sulfonic Acid Sodium (PMAESA) was introduced into the polymers to get sensors with positive charges (ps-pH-positive) or negative charges (ps-pH-negative), while the neutral sensor (ps-pH-neutral) does not possess either of these fractions.

The sensors were polymerized using the traditional radical polymerization approach with co-polymerization of ANNA-HEMA, HPMA and MAETMA or MAESA in DMF where AIBN was used as an initiator. The polymeric pH sensors (ps-pH) were sequentially harvested by precipitation from solvent into acetone and ether. To remove any non-polymerized monomers and other potential chemicals, sensors were dialyzed against deionized water for 48 h before further characterization and application. The sensors were characterized using gel permeation chromatography (GPC). The average molecular weights (Mn) of three kinds of pH sensors were about 4,000 each. The polydispersity indexes (PDI) of three polymers were about 1.5 each. Zeta potential measurement was performed in 10 mM of HEPES buffer (pH 7.4) and indicated 10.1 mV for ps-pH-positive, −1.36 mV for ps-pH-neutral and −11.1 mV for ps-pH-negative, respectively.

Cellular Internalization of the Sensors

After dialysis against deionized water, the aqueous solutions of these sensors were filtered by 40.2 m filter before they were applied to microbial culture. Microbes were incubated with fresh medium containing 10 μg/mL of pH sensor at room temperature for at least 24 h without any disturbance. No inhibition effect on cell growth was observed even after longer incubation. The distribution of sensors in microbial culture was detected by fluorescence imaging with confocal microscopy (FIG. 1A and Figure S1-4). Results showed that ps-pH-neutral and ps-pH-negative were not cell permeable for any of the microbes tested in this experiment, which are *Lactobacillus fermentum* (gram-positive), *E. coli* (gram-negative), *B. subtilis* (gram-positive), and *S. cerevisiae*; while the sensor with positive charges, ps-pH-positive, is partially cell permeable for lactobacilli and yeast since weak fluorescence was observed inside cells.

A similar test was performed with mammalian cells by incubating cells with medium containing 10 μg/mL of sterilized pH sensor at 37° C. for 24 h. Using MitoTracker Red as the positive control, imaging data (FIGS. 1B and 1C and Figure S5-7) shows that neither ps-pH-neutral or ps-pH-negative can be taken up by HeLa cell or MCF-7 cells; while the one with positive charges can get into both cell lines. It is no surprise that the macrophage cell J774 took up all three formats of polymeric pH sensors with its biological function of phagocytosis.

Based on the distribution of the above results, ps-pH-neutral was selected for further characterization and applications in measuring extracellular acidification.

Sensor (Ps-pH-Neutral) Response to pH

Figure 2A:
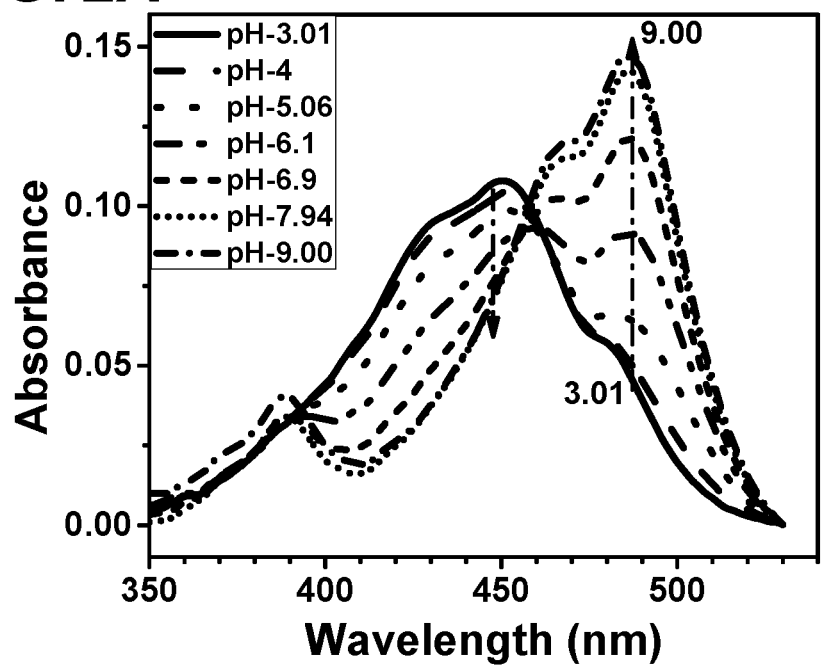
FIGS. 2A-2D show the pH titration for ps-pH neutral.
Figure 2B:
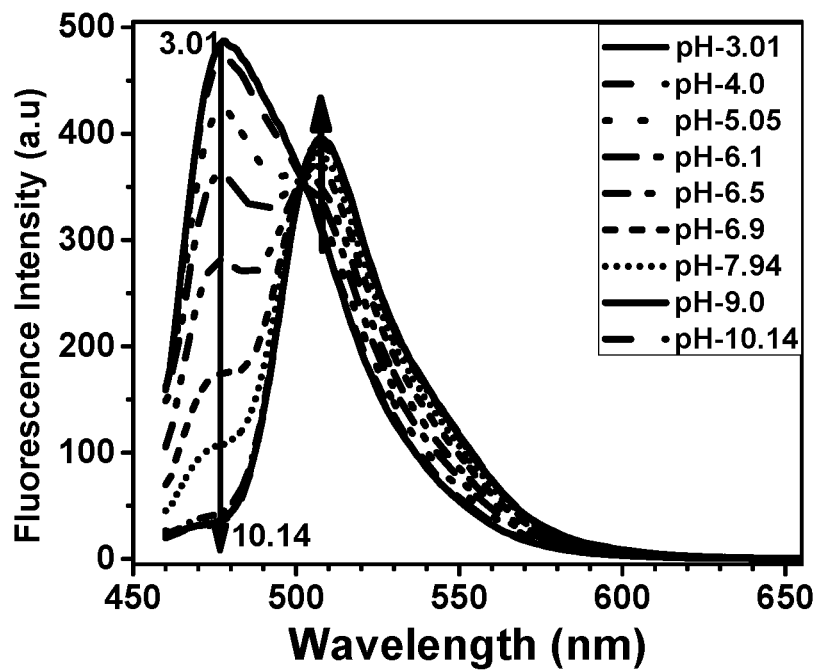
Figure 2C:
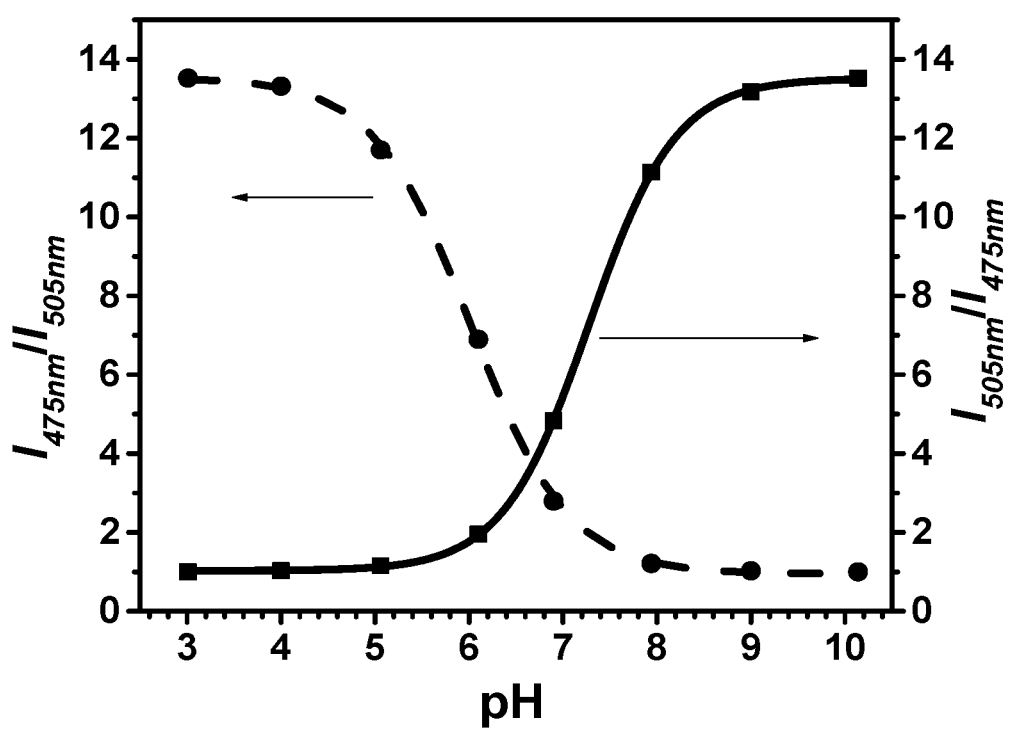
Figure 2D:
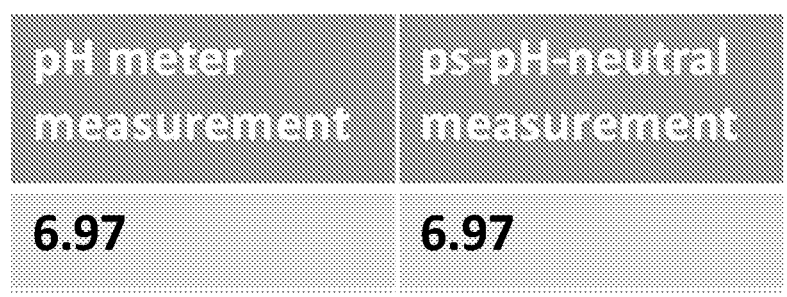

A B—R buffer with pH range 3 to 10 was applied to test the pH responses of the sensor. Similar to the sensing probe ANNA, the polymeric pH sensor shows pH-dependent absorbance spectra with an isosbestic point at 455 nm (FIG. 2A)[41]. The fluorescent emission spectra from the sensor under excitation at the isosbestic e point 455 nm possess two peaks at 475 nm and 505 nm, respectively (FIG. 2B). The ratio of fluorescence intensity at 475 nm to the intensity at 505 nm ($I_{475\,nm}/I_{505\,nm}$ or $I_{505\,nm}/I_{475\,nm}$) was plotted vs pH and the curve was fit with Bolzmann model by OriginPro 9 (FIG. 2B). The curve fitting equation and the related parameters are listed in Table S1. The pH values, which were calculated from fluorescence intensity by fitting the equation of ps-pH-neutral, were validated by a pH meter. The measurement error is less than 0.01. Three concentrations of pH sensors were applied to test the concentration effects on the pH response of sensors. As shown in Figure S8, the three titration curves overlapped very well, indicating that there is not much effect from sensor concentrations on the sensor performances. 10 µg/mL of ps-pH-neutral was used for the next biological experiments.

Application of Ps-pH-Neutral in Bacterial Culture

Figure 3A:
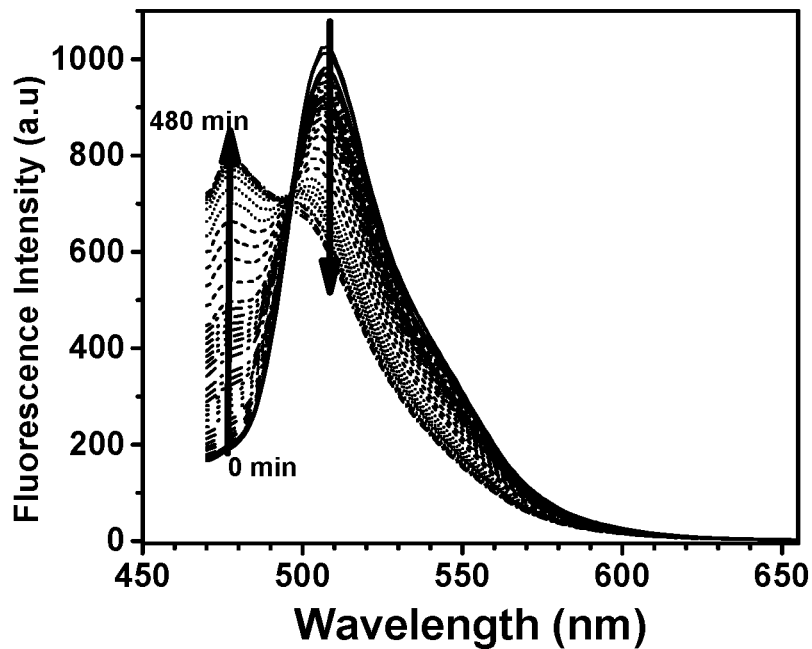
FIGS. 3A-3F show the application of ps-pH-neutral in bacterial culture. Bacterial culture containing pH sensors were incubated in a sealed cuvette at 37° C. The fluorescence spectra of pH sensors were dynamically detected by spectrofluorophotometer under 455 nm excitation, A: *L. fermentum*, C: *E. coli*, E: *B. subtilis*. The pH values (marks beginning at upper left) were transferred from their corresponding spectra data and were plotted together with their growth curve (marks beginning at lower left mark), B: *L. fermentum*, D: *E. coli*, F: *B. subtilis*.
Figure 3B:
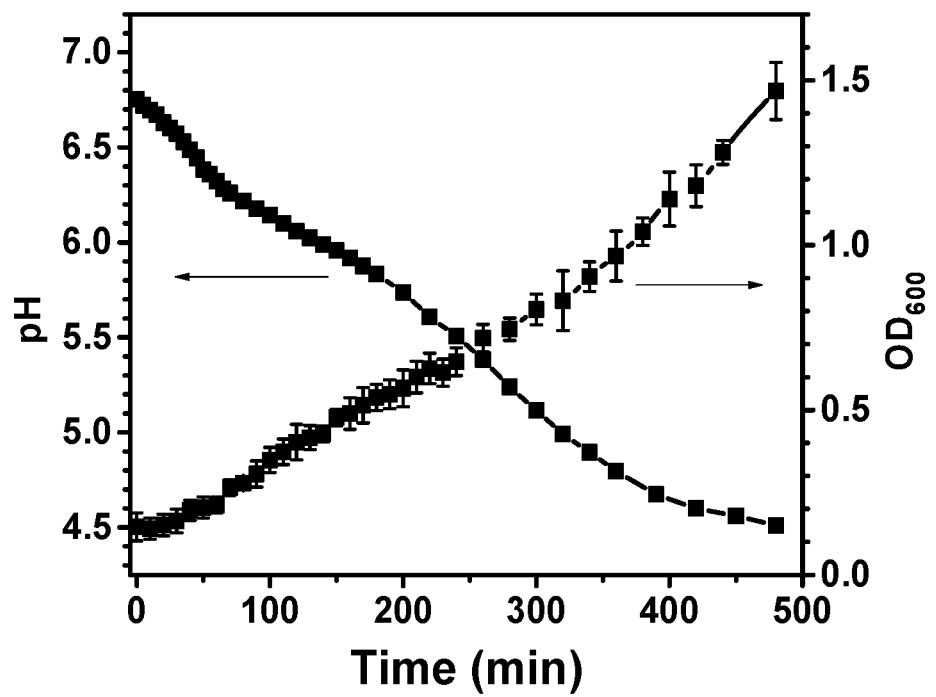
Figure 3C:
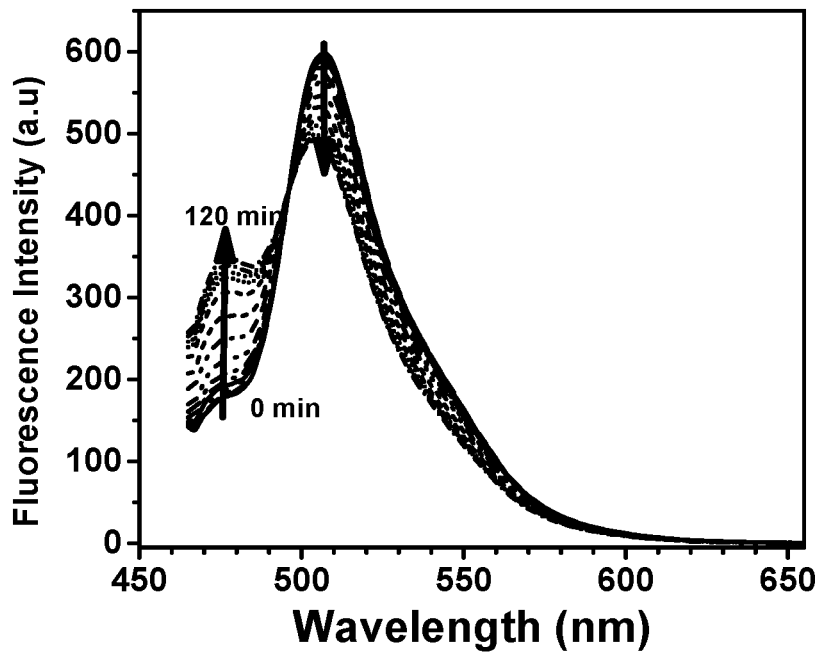

The application of ps-pH-neutral was tested with three kinds of bacteria, i.e. *L. fermentum, B. subtilis*, and *E. coli*, which represent the most commonly used bacteria in their related biology and biotechnology fields (Table 1). Cuvette and 96-well microplate were applied for low throughput studies (FIG. 3) and high throughput studies (FIG. 4) under the sealed condition with mineral oil, respectively. In the low throughput studies, bacterial culture with pH sensor was incubated at 37° C. The pH responding spectra in the 2 mL cuvette were collected by spectrofluorophotometer under the excitation of 455 nm (FIGS. 3A, 5C, and 5E). The pH responses of the sensor were also tested in a 96-well microplate to demonstrate the capacity for high throughput applications, where multiple concentrations of bacteria were repeatedly seeded in wells. The fluorescent emission at 475 nm and 505 nm from each well could be efficiently detected by a microplate reader with two-minute intervals (FIGS. 4A, 4C and 4E). Besides the bacteria concentration used in low throughput study (0.1 $OD_{600}$), higher concentrations of bacteria (0.2, 0.3 or 0.4 $OD_{600}$) were also tested in the high throughput study.

Figure 3D:
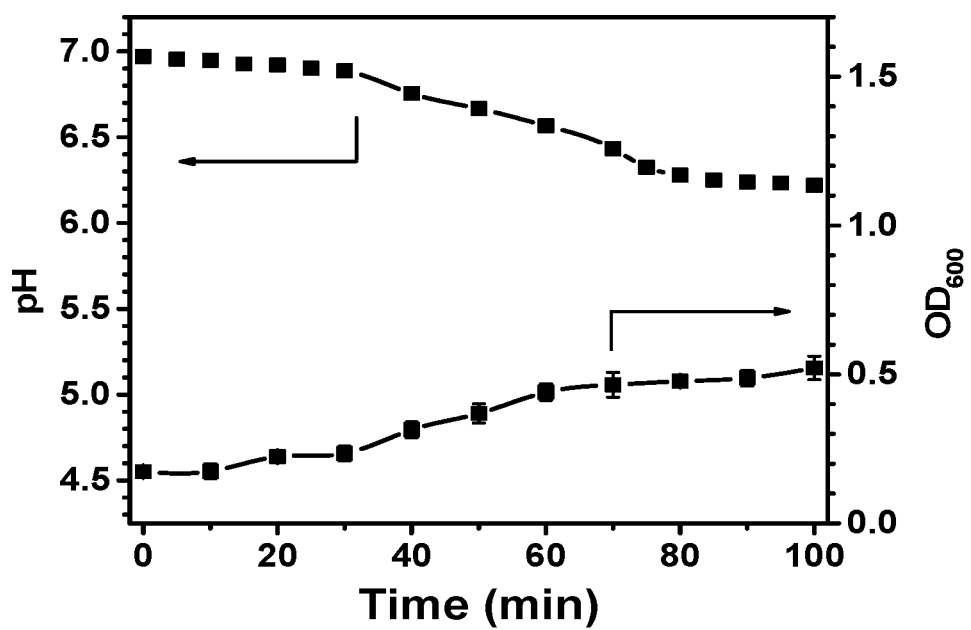
Figure 4C:
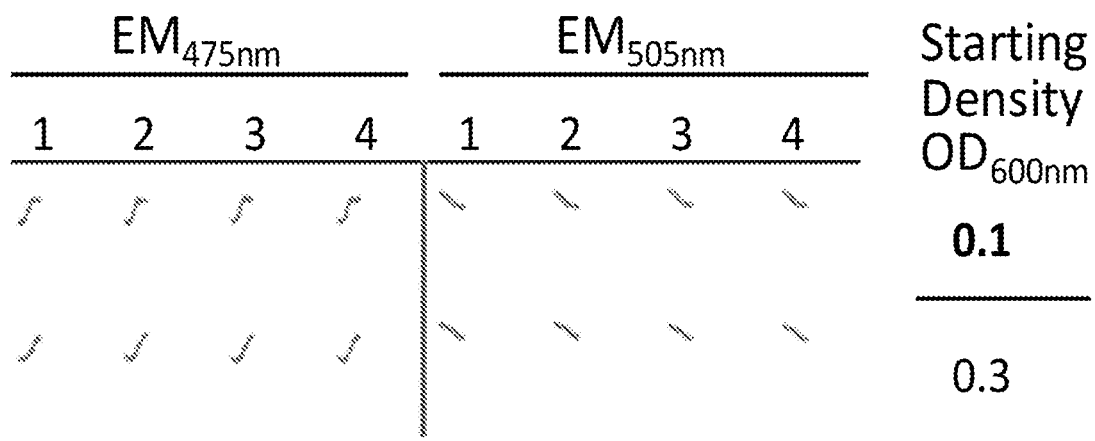
Figure 4D:
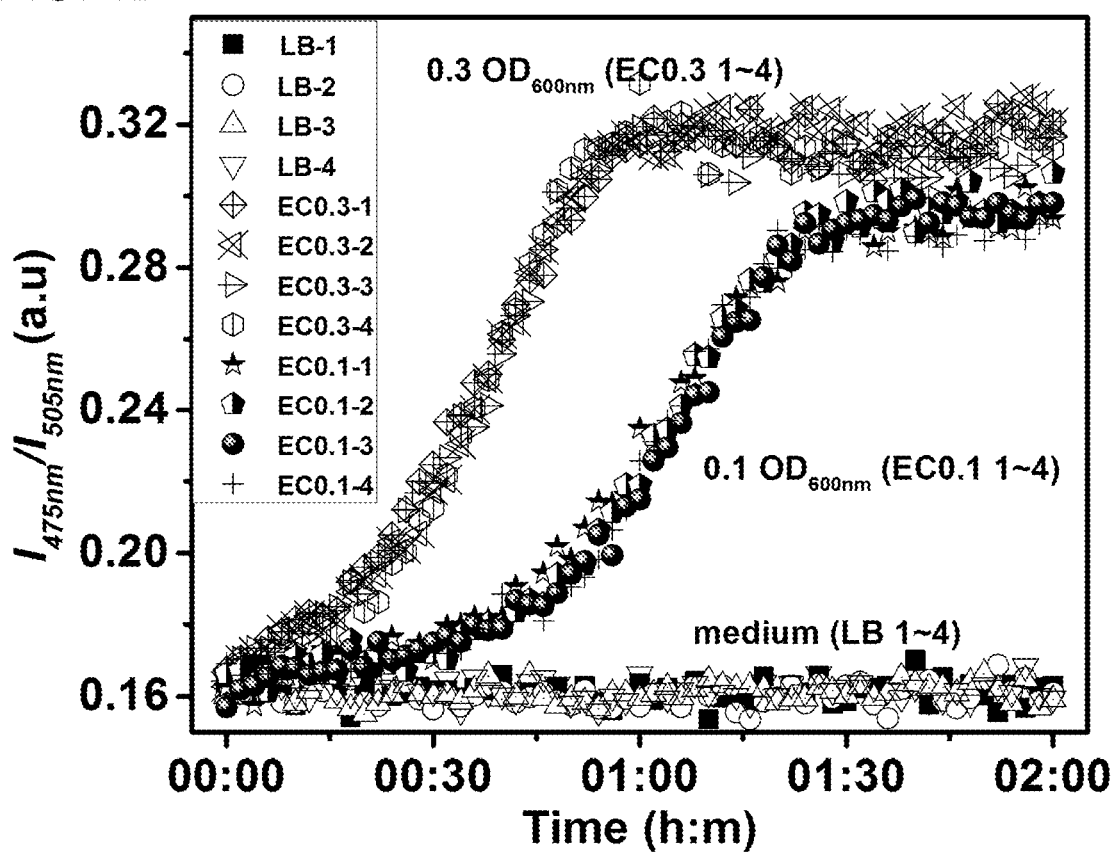
Figure 4E:
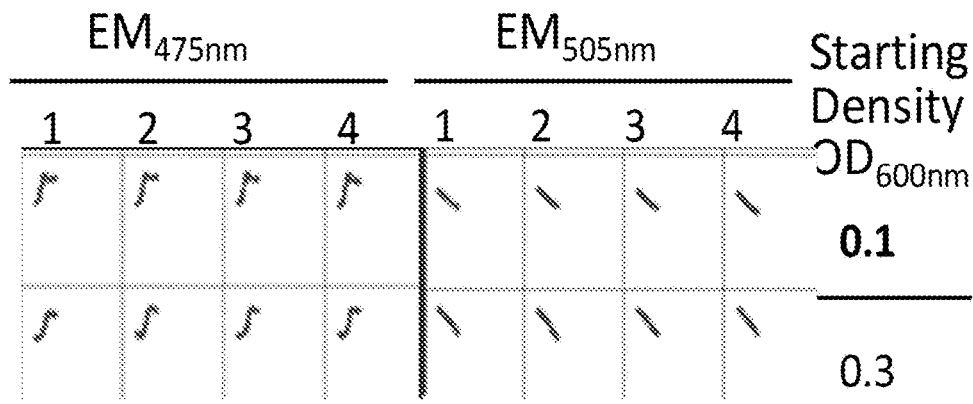

*L. fermentum* is a Gram-positive, heterofermentative lactic acid bacterium which is wildly used in the production of fermented food[53]. It was reported that the pH of *L. fermentum* culture dramatically affects the product of fermentation[54]. It has been also used as a probiotic with its functional efficacy of antimicrobial and antioxidative activities[55, 56]. During the incubation, the fluorescent intensity at 475 nm continued increasing, while the intensity at 505 nm continued decreasing (FIG. 3A), meaning the cultural environment was acidized by lactobacilli under an anaerobic condition. The pH values of the cellular culture, which were calculated from the ratios of $I_{475\ nm}/I_{505\ nm}$, changed from 6.75 to 4.51 during the cell growth from 0.15 to 1.47 $OD_{600}$ (FIG. 3B). Three concentrations of lactobacilli, i.e. 0.1, 0.2 and 0.4 $OD_{600}$, were applied in high throughput studies. As shown in FIG. 4A, fluorescent emission at 475 nm and 505 nm from each well could be efficiently detected by a microplate reader. The ratio data from the same condition shows consistency throughout the experiment (FIG. 4B).

emission peaks (FIG. 3C), was changed from 6.97 to 6.22, when the density of bacteria was changed from 0.17 to 0.52 $OD_{600}$ (FIG. 3D). Two starting bacterial densities, i.e. 0.1 and 0.3 $OD_{600}$, were used in the high throughput test (FIG. 4C). During two hours of incubation at 37° C., each well with the same condition showed a very similar ratio of fluorescence emission at 475 nm to emission at 505 nm at each time point (FIG. 4D).

Figure 3E:
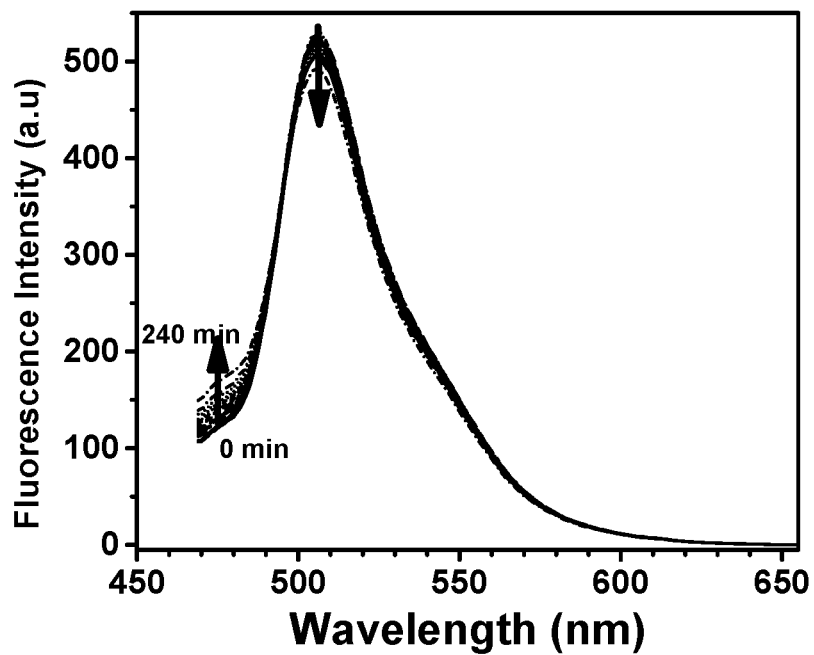
Figure 3F:
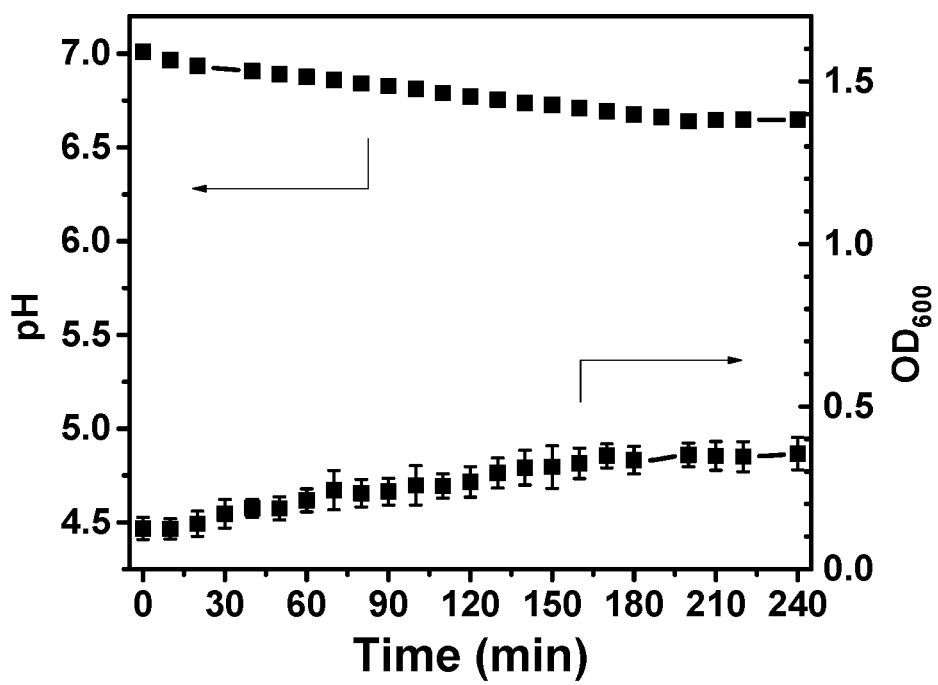
Figure 4F:
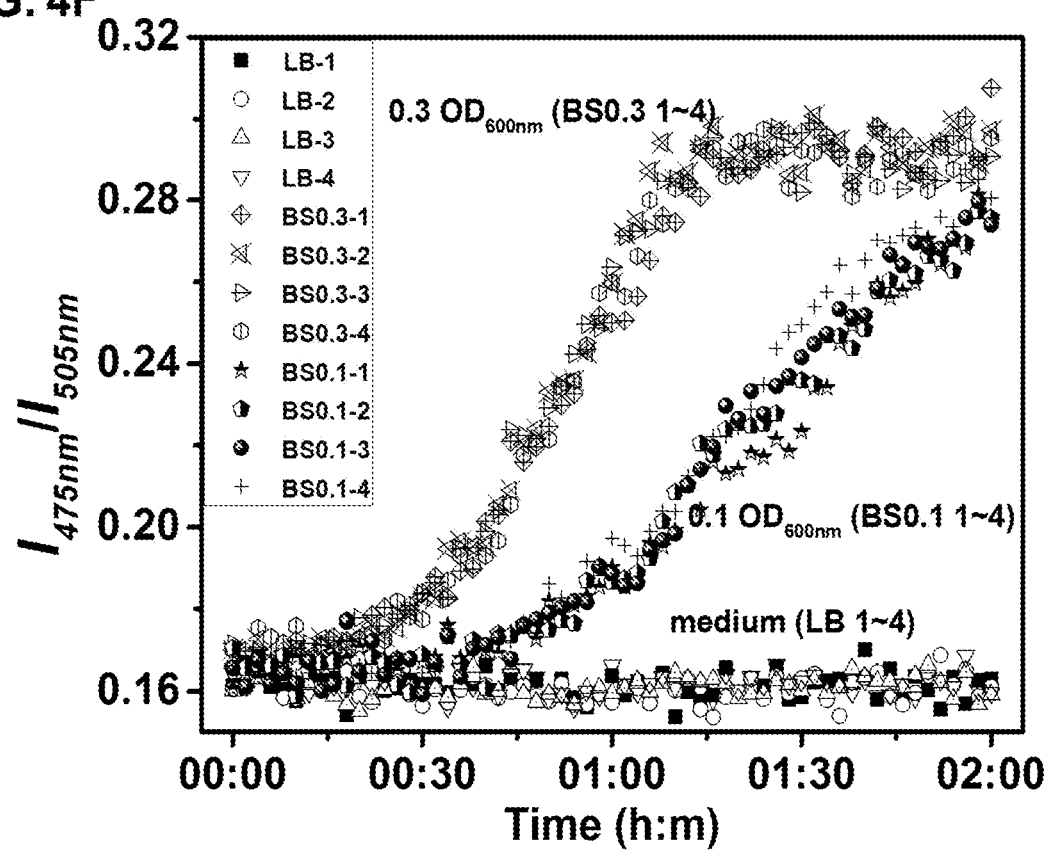

*B. subtilis* is the best studied Gram-positive facultative anaerobe that has been widely used as the paradigm of Gram-positive bacteria. The metabolism of *B. subtilis*, which is very sensitive to environmental pH, has been intensively investigated[60-62]. *B. subtilis* is one of the most commonly used industrial bacterium to produce enzymes and other metabolites. The product of anaerobic fermentation of *B. subtilis* includes 2,3-butanediol, ethanol and acetate[63]. *B. subtilis* were cultured under aerobic conditions. When they were seeded in an environment where the oxygen supply was blocked and residual oxygen in the medium was consumed very quickly[26], the pH of the culture did not change much, i.e. from 7.01 to 6.65 (FIGS. 3E and 3F). The optical density of bacteria ($OD_{600}$) only grew from 0.12 to 0.35 in four hours of incubation. In the microplate, the ratios of fluorescence intensity at 455 nm and 505 nm (FIG. 4E), is relatively stable and repeatable among wells with the same starting condition, 0.1 or 0.3 $OD_{600}$ (FIG. 4F).

Because of the different metabolites produced by bacteria under anaerobic conditions (Table 1), the pH of these three bacterial cultures changed with different trends during incubation. With the well-known capability to produce lactic acid, the pH of *L. fermentum* culture can reach even lower pH than 4.5 (data not shown). Under the experimental condition applied on *B. subtilis*, there was about 0.35 pH change detected by our pH sensor. Because of different metabolic pathways under anaerobic condition, the pH changes in different trends among three bacterial cultures tested in this experiment (FIG. 4). Especially for *E. coli* and *B. subtilis*, which are normally cultured in aerobic condition, data detected by ps-pH-neutral in microplates show that the extracellular pHs changed with different rates when they were sealed in the same space with limited oxygen supply, and the same thing happened to two concentrations of the same bacteria (FIGS. 4D and 6F). Besides the excellent reproducibility of the sensor for high throughput applica-

TABLE 1

Bacteria used in the testing of pH sensors.

| Bacterium | Gram reaction | Metabolism | Main products of fermentation | References |
| --- | --- | --- | --- | --- |
| L. fermentum | positive | facultative anaerobic | lactic acid, ethanol, $CO_2$ | 53, 54 |
| E. coli | negative | facultative anaerobic | acetate, ethanol etc. | 57-59 |
| B. subtilis | positive | facultative anaerobic | 2,3-butanediol, ethanol and acetate. | 60-63 |

*E. coli* is a Gram-negative, facultative anaerobe. It is the best studied bacterium and the most common bacteria used in lab cloning and also one of the preferred bacteria for research on regulation of metabolism 57[5]. Its respiratory pathways can be alternatively switched to cater to the energy request under different culture conditions. The anaerobic metabolism produces acetate, ethanol and $CO_2$ etc. into the microenvironment. It has been reported that environmental pH affects the fermentation and plasmid product 5[9]. The pH of *E. coli* culture, which was transformed from the ratio of tions, it is worth noting that the pH sensor shows good photo-stability during incubation, and no obvious photo-bleaching effect was detected (fluorescent ratio cure of medium, FIGS. 4B, 4D and 4F).

Application of Ps-pH-Neutral in *S. cerevisiae* Culture

Figure 5A:
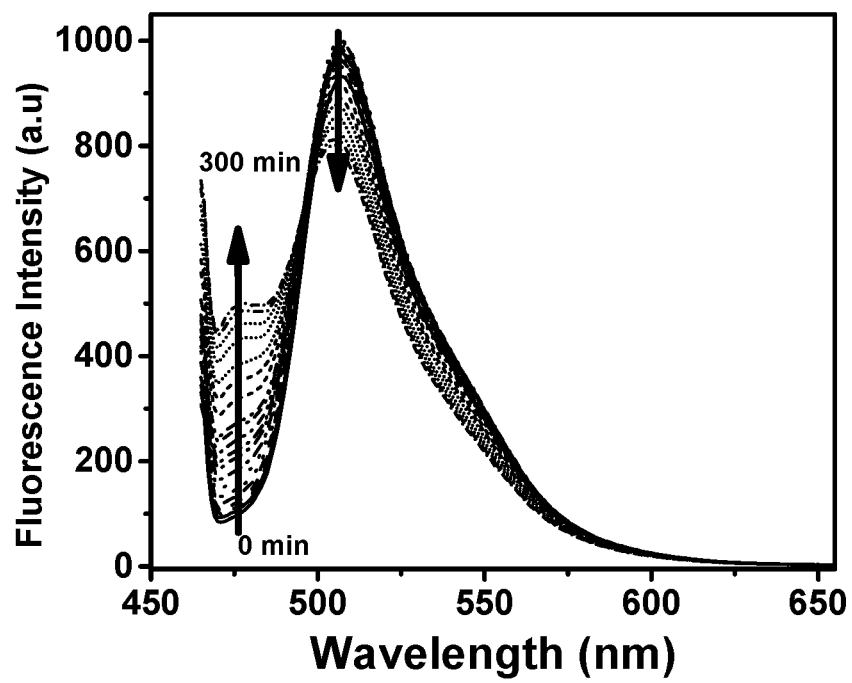
Figure 5B:
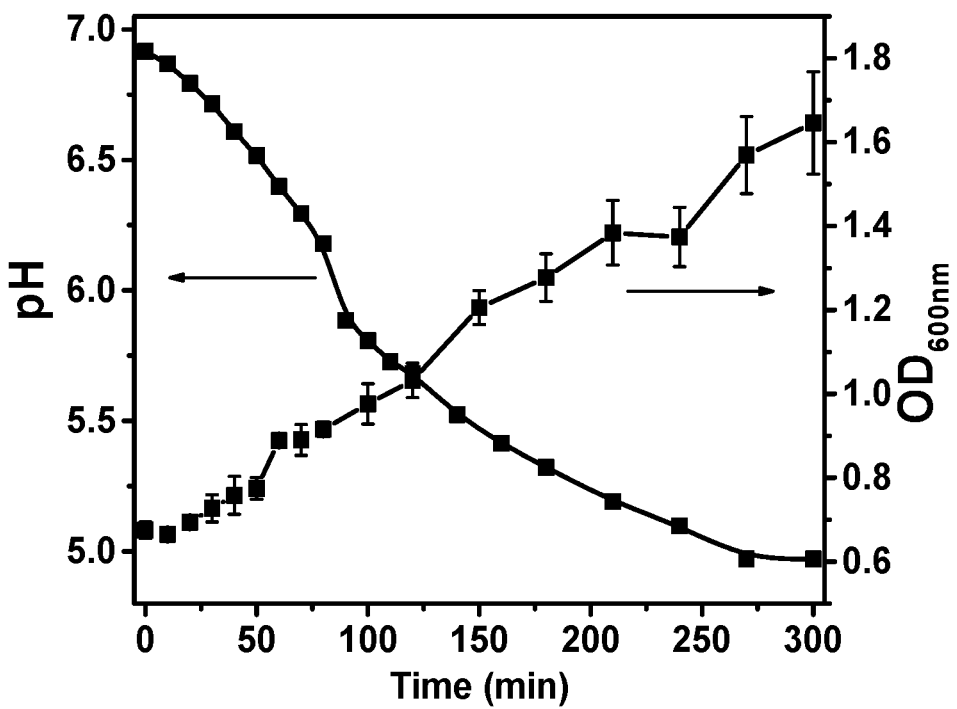

*S. cerevisiae* is the most widely used microbe in the bioindustry including the food and beverage industry, bioethanol production and other fine chemical production[64]. Environmental pH has a strong effect on the growth and fermentation property of *S. cerevisiae*[65-67] The application of the pH sensor in monitoring pH of *S. cerevisiae* culture was performed both in a cuvette and a 96-well microplate where the oxygen supply was blocked to introduce an anaerobic cell culture environment. To observe a conspicuous change of fluorescence, 0.65 $OD_{600}$ starting density of yeast were sealed in the cuvette and were incubated with the pH sensor at 30° C. for five hours to detect the pH and optical density of culture, respectively (FIGS. 5A and 5B). As a eukaryotic organism which can grow under anaerobic conditions, the density of *S. cerevisiae* reached 1.65 $OD_{600}$, while the pH of the culture was acidized from 6.91 to 4.97. To test the sensor response to pH in a high-throughput platform, three starting densities, 0.1, 0.3 and 0.6 $OD_{600}$, of yeast were quadruplicately applied in 96-well plate (FIG. 5C). During six hours of incubation, the ratios of fluorescence intensity at 475 nm and 505 nm, which were detected by microplate reader under excitation 455 nm, are well correlated with their culture conditions (FIG. 5D). Signal vibration was observed at the late incubation. It might be the result of releasing $CO_2$ from culture, which is one of the main products of fermentation with *S. cerevisiae*.

Besides using microbes, the ability of the pH sensor (ps-pH-neutral) to monitor extracellular pH of mammalian cells was preliminarily tested in a standard 96-well microplate. When cells grew to 90% confluence, cell culture medium in each well was substituted by medium which was adjusted to different pH values (medium-pH) containing 10 µg/mL of pH sensors (Figure S10A). The fluorescence spectra in each well were detected by a microplate reader under 440 nm, 480 nm and 455 nm excitation, respectively (Figure S10B). As we can see from fluorescence spectra in Figures S10B and S10C, each well had a good spectrum corresponding to the related pH condition. This result shows us the very promising capability of the pH sensor (ps-pH-neutral) to test multiple conditions of mammalian cells with a standard 96-well plate. No obvious cytotoxicity to mammalian cells (HeLa MCF-7 and J-774c cells, respectively) was observed after 24 h of incubation with culture medium containing 10 µg/mL of the pH sensor (Figure S11).

CONCLUSION

A new water-soluble polymer-based pH sensor was developed to specifically detect extracellular pH. The varying responses of two fluorescence emission peaks (475 nm and 505 nm) under 455 nm excitation enables the sensor to ratiometrically detect pH with high accuracy. The biocompatible polymer, i.e. PHPMA, was introduced into the sensor to improve the water solubility. After 96 h of incubation of cells with sensor (ps-pH-neutral), no inhibition to cell growth was observed (data not shown). Tested with Gram-negative bacteria (*E. coli*), Gram-positive bacteria (*L. fermentum* and *B. subtilis*), yeast (*S. cerevisiae*) and mammalian cells (HeLa and MCF-7), the pH sensor, ps-pH-neutral, has been proven to be exclusively extracellularly localized. This is critical to detect the environmental pH of cells. All of these characteristics ensure the pH sensor can be conveniently used to detect cell metabolism with minimal disturbance to cells.

The reliable performance in the detection of pH changes in a microplate further characterized ps-pH-neutral as a powerful tool in high-throughput screens (HTC) with a commercial microplate reader, which is widely used in drug discovery, optimization of reactions, etc. With assistance of a high resolution imaging instrument, this pH sensor has high potential to be used in single cell metabolism assays 68 The following references are incorporated by reference in their entireties:

1. I. R. Booth, T. A. Krulwich, E. Padan, J. B. Stock, G. M. Cook, V. Skulachev, G. N. Bennett, W. Epstein, J. L. Slonczewski, R. J. Rowbury, A. Matin, J. W. Foster, R. K. Poole, W. N. Konings, G. Schafer and P. Dimroth, *Novart Fdn Symp*, 1999, 221, 19-37.
2. J. R. Casey, S. Grinstein and J. Orlowski, *Nat Rev Mol Cell Bio*, 2010, 11, 50-61.
3. T. A. Krulwich, G. Sachs and E. Padan, *Nat Rev Microbiol*, 2011, 9, 330-343.
4. I. H. Madshus, *Biochem J*, 1988, 250, 1-8.
5. V. A. Ruffin, A. I. Salameh, W. F. Boron and M. D. Parker, *Front Physiol*, 2014, 5, 43.
6. R. A. Cairns, I. S. Harris and T. W. Mak, *Nat Rev Cancer*, 2011, 11, 85-95.
7. R. A. Gatenby and R. J. Gillies, *Nat Rev Cancer*, 2004, 4, 891-899.
8. Y. Kato, S. Ozawa, C. Miyamoto, Y. Maehata, A. Suzuki, T. Maeda and Y. Baba, *Cancer Cell Int*, 2013, 13, 89.
9. L. M. Prescott, J. P. Harley and D. A. Klein, Microbiology, McGraw-Hill Higher Education, Dubuque, Iowa, 6th edn., 2005.
10. R. K. Thauer, K. Jungermann and K. Decker, *Bacteriol Rev*, 1977, 41, 100-180.
11. E. K. Rofstad, B. Mathiesen, K. Kindem and K. Galappathi, *Cancer Res*, 2006, 66, 6699-6707.
12. V. Estrella, T. A. Chen, M. Lloyd, J. Wojtkowiak, H. H. Comnell, A. Ibrahim-Hashim, K. Bailey, Y. Balagurunathan, J. M. Rothberg, B. F. Sloane, J. Johnson, R. A. Gatenby and R. J. Gillies, *Cancer Res*, 2013, 73, 1524-1535.
13. A. Jagielska, K. D. Wilhite and K. J. Van Vliet, *Plos One*, 2013, 8, e76048.
14. L. Xu, D. Fukumura and R. K. Jain, *J Biol Chem*, 2002, 277, 19242-19242.
15. A. Lardner, *J Leukocyte Biol*, 2001, 69, 522-530.
16. A. L. Teo, A. Mantalaris and M. Lim, *Biochem Eng J*, 2014, 90, 8-15.
17. S. H. Kim and G. M. Lee, *J Microbiol Biotechn*, 2007, 17, 712-720.
18. F. N. Arroyo-Lopez, S. Orlic, A. Querol and E. Barrio, *Int J Food Microbiol*, 2009, 131, 120-127.
19. Y. Lin, W. Zhang, C. J. Li, K. Sakakibara, S. Tanaka and H. N. Kong, *Biomass Bioenerg*, 2012, 47, 395-401.
20. J. Liu, Q. Wang, H. Zou, Y. Liu, J. Wang, K. Gan and J. Xiang, *Microb Biotechnol*, 2013, 6, 685-693.
21. J. Piontek, M. Lunau, N. Handel, C. Borchard, M. Wurst and A. Engel, *Biogeosciences*, 2010, 7, 1615-1624.
22. K. A. Weber, L. A. Achenbach and J. D. Coates, *Nat Rev Microbiol*, 2006, 4, 752-764.
23. J. D. Erfle, R. J. Boila, R. M. Teather, S. Mahadevan and F. D. Sauer, *J Dairy Sci*, 1982, 65, 1457-1464.
24. Y. Tian, E. Fuller, S. Klug, F. Lee, F. Su, L. Zhang, S. H. Chao and D. R. Meldrum, *Sensors and actuators. B, Chemical*, 2013, 188, 1-10.
25. L. Zhang, F. Su, S. Buizer, X. Kong, F. Lee, K. Day, Y. Tian and D. R. Meldrum, *Chemical communications (Cambridge, England)*, 2014, 50, 6920-6922.
26. L. Zhang, F. Su, S. Buizer, H. Lu, W. Gao, Y. Tian and D. Meldrum, *Biomaterials*, 2013, 34, 9779-9788.
27. H. Lu, Y. Jin, Y. Tian, W. Zhang, M. R. Holl and D. R. Meldrum, *J Mater Chem*, 2011, 2011, 19293-192301.
28. Y. Tian, F. Su, W. Weber, V. Nandakumar, B. R. Shumway, Y. Jin, X. Zhou, M. R. Holl, R. H. Johnson and D. R. Meldrum, *Biomaterials*, 2010, 31, 7411-7422.

29. Y. Li, Y. Wang, S. Yang, Y. Zhao, L. Yuan, J. Zheng and R. Yang, *Anal Chem,* 2015, 87, 2495-2503.
30. J. Qi, D. Liu, X. Liu, S. Guan, F. Shi, H. Chang, H. He and G. Yang, *Anal Chem,* 2015, 87, 5897-5904.
31. L. Yang, N. Li, W. Pan, Z. Yu and B. Tang, *Anal Chem,* 2015, 87, 3678-3684.
32. S. Nagl and O. S. Wolfbeis, *Analyst,* 2007, 132, 507-511.
33. J. Yin, Y. Hu and J. Yoon, *Chem Soc Rev,* 2015, 44, 4619-4644.
34. J. Ling, G. Naren, J. Kelly, T. S. Moody and A. P. de Silva, *J Am Chem Soc,* 2015, 137, 3763-3766.
35. K. Paek, H. Yang, J. Lee, J. Park and B. J. Kim, *Acs Nano,* 2014, 8, 2848-2856.
36. G. Ke, Z. Zhu, W. Wang, Y. Zou, Z. Guan, S. Jia, H. Zhang, X. Wu and C. J. Yang, *ACS Appl Mater Interfaces,* 2014, 6, 15329-15334.
37. I. Parolini, C. Federici, C. Raggi, L. Lugini, S. Palleschi, A. De Milito, C. Coscia, E. Iessi, M. Logozzi, A. Molinari, M. Colone, M. Tatti, M. Sargiacomo and S. Fais, *J Biol Chem,* 2009, 284, 34211-34222.
38. S. Peppicelli, F. Bianchini and L. Calorini, *Cancer Metastasis Rev,* 2014, 33, 823-832.
39. J. F. Valenzuela, L. Pinuer, A. G. Cancino and R. B. Yanez, *Appl Microbiol Biot,* 2015, 99, 6417-6429.
40. C. Moon, S. Jang, Y. M. Yun, M. K. Lee, D. H. Kim, W. S. Kang, S. S. Kwak and M. S. Kim, *Bioresource Technol,* 2015, 179, 595-601.
41. J. Zhou, C. Fang, T. Chang, X. Liu and D. Shangguan, *J Mater Chem B,* 2013, 1, 661-667.
42. B. K. Grillo-Hill, B. A. Webb and D. L. Barber, *Method Cell Biol,* 2014, 123, 429-448.
43. R. C. Somers, R. M. Lanning, P. T. Snee, A. B. Greytak, R. K. Jain, M. G. Bawendi and D. G. Nocera, *Chem Sci,* 2012, 3, 2980-2985.
44. T. Jin, A. Sasaki, M. Kinjo and J. Miyazaki, *Chem Commun,* 2010, 46, 2408-2410.
45. L. Long, X. Li, D. Zhang, S. Meng, J. Zhang, X. Sun, C. Zhang, L. Zhou and L. Wang, *Rsc Adv,* 2013, 3, 12204-12209.
46. T. M. Cannon, A. T. Shah, A. J. Walsh and M. C. Skala, *J Biomed Opt,* 2015, 20.
47. W. F. An and N. Tolliday, *Mol Biotechnol,* 2010, 45, 180-186.
48. Y. Zhao, Q. Hu, F. Cheng, N. Su, A. Wang, Y. Zou, H. Hu, X. Chen, H. M. Zhou, X. Huang, K. Yang, Q. Zhu, X. Wang, J. Yi, L. Zhu, X. Qian, L. Chen, Y. Tang, J. Loscalzo and Y. Yang, *Cell Metab,* 2015, 21, 777-789.
49. M. Musken, S. Di Fiore, U. Romling and S. Haussler, *Nat Protoc,* 2010, 5, 1460-1469.
50. H. Lu, F. Su, Q. Mei, Y. Tian, W. Tian, R. H. Johnson and D. R. Meldrum, *J Mater Chem,* 2012, 22, 9890-9900.
51. A. Kelsch, S. Tomcin, K. Rausch, M. Barz, V. Mailander, M. Schmidt, K. Landfester and R. Zentel, *Biomacromolecules,* 2012, 13, 4179-4187.
52. T. Lammers and K. Ulbrich, *Adv Drug Deliver Rev,* 2010, 62, 119-121.
53. S. Jayashree, S. Pooja, M. Pushpanathan, U. Vishnu, J. Sankarasubramanian, J. Rajendhran and P. Gunasekaran, *Genome Announc,* 2013, 1, e00770-13.
54. M. C. Santoyo, G. Loiseau, R. R. Sanoja and J. P. Guyot, *Int J Food Microbiol,* 2003, 80, 77-87.
55. M. Mikelsaar and M. Zilmer, *Microb Ecol Health Dis,* 2009, 21, 1-27.
56. G. Reid, *Appl Environ Microbiol,* 1999, 65, 3763-3766.
57. Y. Dharmadi, A. Murarka and R. Gonzalez, *Biotechnol Bioeng,* 2006, 94, 821-829.
58. G. Unden and J. Bongaerts, *Biochim Biophys Acta,* 1997, 1320, 217-234.
59. J. T. Cortes, N. Flores, F. Bolivar, A. R. Lara and O. T. Ramirez, *Biotechnol Bioeng,* 2015, 113, 598-611.
60. A. L. Sonenshein, *Nat Rev Microbiol,* 2007, 5, 917-927.
61. J. M. Buescher, W. Liebermeister, M. Jules, M. Uhr, J. Muntel, E. Botella, B. Hessling, R. J. Kleijn, L. Le Chat, F. Lecointe, U. Mader, P. Nicolas, S. Piersma, F. Rugheimer, D. Becher, P. Bessieres, E. Bidnenko, E. L. Denham, E. Dervyn, K. M. Devine, G. Doherty, S. Drulhe, L. Felicori, M. J. Fogg, A. Goelzer, A. Hansen, C. R. Harwood, M. Hecker, S. Hubner, C. Hultschig, H. Jarmer, E. Klipp, A. Leduc, P. Lewis, F. Molina, P. Noirot, S. Peres, N. Pigeonneau, S. Pohl, S. Rasmussen, B. Rinn, M. Schaffer, J. Schnidder, B. Schwikowski, J. M. Van Dijl, P. Veiga, S. Walsh, A. J. Wilkinson, J. Stelling, S. Aymerich and U. Sauer, *Science,* 2012, 335, 1099-1103.
62. J. C. Wilks, R. D. Kitko, S. H. Cleeton, G. E. Lee, C. S. Ugwu, B. D. Jones, S. S. BonDurant and J. L. Slonczewski, *Appl Environ Microb,* 2009, 75, 981-990.
63. H. Cruz Ramos, T. Hoffmann, M. Marino, H. Nedjari, E. Presecan-Siedel, O. Dreesen, P. Glaser and D. Jahn, *J Bacteriol,* 2000, 182, 3072-3080.
64. E. Nevoigt, *Microbiol Mol Biol R,* 2008, 72, 379-412.
65. X. Liu, B. Jia, X. Sun, J. Ai, L. Wang, C. Wang, F. Zhao, J. Zhan and W. Huang, *J Food Sci,* 2015, 80, M800-808.
66. M. K. Nielsen and N. Arneborg, *Food Microbiol,* 2007, 24, 101-105.
67. A. Pena, N. S. Sanchez, H. Alvarez, M. Calahorra and J. Ramirez, *Fems Yeast Res,* 2015, 15, fou005.
68. M. E. Lidstrom and D. R. Meldrum, *Nat Rev Microbiol,* 2003, 1, 158-164.

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

What is claimed is:

1. A fluorescent pH sensor comprising a copolymer, wherein the copolymer comprises:
   (a) a polymerized form of a probe for sensing pH; and
   (b) a polymerized form of N-(2-hydroxypropyl)methacrylamide (HPMA) or 2-hydroxyethyl methacrylate (HEMA);
   wherein:
   the probe for sensing pH has formula (I):

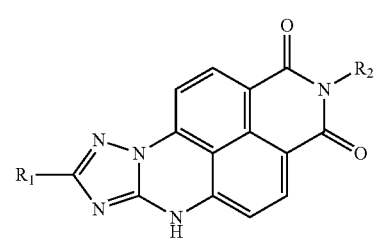

wherein
$R_1$ is selected from H, $(C_1-C_{12})$haloalkyl, $(C_1-C_{12})$perhaloalkyl, or $(C_1-C_{12})$alkyl, wherein said $(C_1-C_{12})$alkyl is unsubstituted or substituted with one or more substituents selected from the group consisting of $NH_2$, $NH(C_1-C_6)$alkyl, OH, $O(C_1-C_6)$alkyl, SH and $S(C_1-C_6)$alkyl;

$R_2$ is $(C_mH_{2m}—X)_a—C_nH_{2n}—Y$;

m is an integer selected from the group consisting of 1, 2, 3, 4, 5, 6, 7, 8, 9 and 10;

n is an integer selected from the group consisting of 0, 1, 2, 3, 4, 5, 6, 7, 8, 9 and 10;

a is an integer selected from the group consisting of 1, 2, 3, 4, 5, 6, 7, 8, 9 and 10;

X is selected from O, C(=O)O, C(=O)NH, C(=O)N($C_1-C_6$)alkyl and OC(=O);

Y is selected from:

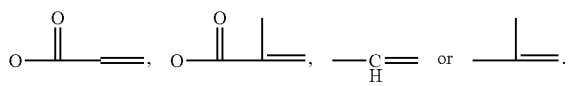

2. The fluorescent pH sensor of claim 1, further comprising (c) a polymerized form of monomer having a negative charge.

3. The fluorescent pH sensor of claim 2, wherein the monomer having a negative charge is 2-(methacryloyloxy)ethylsulfonic acid (MESA).

4. The fluorescent pH sensor of claim 1, further comprising (d) a polymerized form of monomer having a positive charge.

5. The fluorescent pH sensor of claim 4, wherein the monomer having a positive charge is [2-(methacryloyloxy)ethyl]trimethylammonium chloride (MAETMA).

6. The fluorescent pH sensor of claim 1, wherein, in the probe for sensing pH, $R_1$ is H.

7. The fluorescent pH sensor of claim 1, wherein, in the probe for sensing pH, $R_2$ is $C_mH_{2m}—C(=O)O—C_nH_{2n}—Y$.

8. The fluorescent pH sensor of claim 7, wherein m is 5.

9. The fluorescent pH sensor of claim 8, wherein n is 2.

10. The fluorescent pH sensor claim 8, wherein Y is

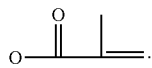

11. The fluorescent pH sensor of claim 7, wherein n is 2.

12. The fluorescent pH sensor of claim 11, wherein Y is

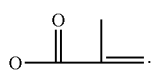

13. The fluorescent pH sensor claim 7, wherein Y is

14. A method of preparing a fluorescent pH sensor, wherein the method comprises the step of:
(a) copolymerizing a probe for sensing pH and a host polymer in the presence of an initiator;
wherein the probe for sensing pH has formula (I):

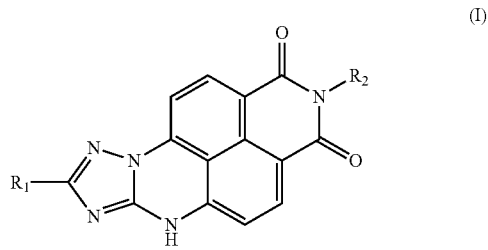

wherein
$R_1$ is selected from H, $(C_1-C_{12})$haloalkyl, $(C_1-C_{12})$perhaloalkyl, or $(C_1-C_{12})$alkyl, wherein said $(C_1-C_{12})$alkyl is unsubstituted or substituted with one or more substituents selected from the group consisting of $NH_2$, $NH(C_1-C_6)$alkyl, OH, $O(C_1-C_6)$alkyl, SH and $S(C_1-C_6)$alkyl;

$R_2$ is $(C_mH_{2m}—X)_a—C_nH_{2n}—Y$;

m is an integer selected from the group consisting of 1, 2, 3, 4, 5, 6, 7, 8, 9 and 10;

n is an integer selected from the group consisting of 0, 1, 2, 3, 4, 5, 6, 7, 8, 9 and 10;

a is an integer selected from the group consisting of 1, 2, 3, 4, 5, 6, 7, 8, 9 and 10;

X is selected from O, C(=O)O, C(=O)NH, C(=O)N($C_1-C_6$)alkyl and OC(=O);

Y is selected from:

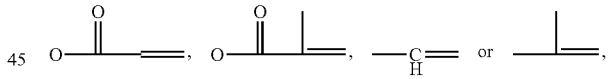

15. The method of claim 14, wherein the initiator is a thermal initiator.

16. The method of claim 15, wherein the thermal initiator is 2,2'-azobis(2-methylpropionitrile) (AIBN).

17. The method of claim 14, wherein the host polymer is HPMA.

\* \* \* \* \*